Figure 1A:
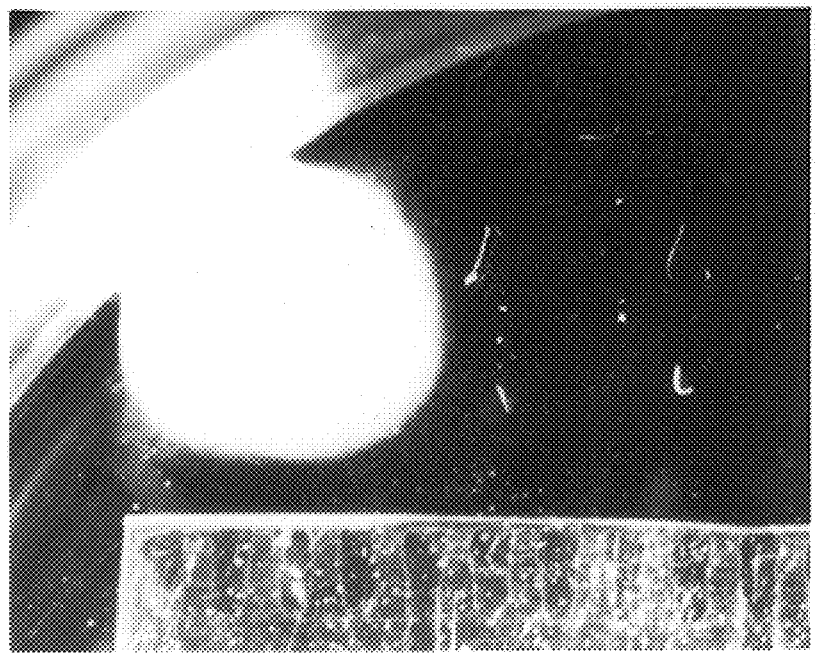

United States Patent [19]
Purchio et al.

[11] Patent Number: 5,919,702
[45] Date of Patent: Jul. 6, 1999

[54] PRODUCTION OF CARTILAGE TISSUE USING CELLS ISOLATED FROM WHARTON'S JELLY

[75] Inventors: Anthony F. Purchio, La Jolla; Brian A. Naughton, El Cajon; Julia San Román, San Diego, all of Calif.

[73] Assignee: Advanced Tissue Science, Inc., La Jolla, Calif.

[21] Appl. No.: 08/735,620

[22] Filed: Oct. 23, 1996

[51] Int. Cl.$^6$ ............................... C12N 5/00; C12N 5/02; A01N 63/00

[52] U.S. Cl. ..................... 435/378; 435/366; 435/377; 435/325; 424/93.1

[58] Field of Search ..................... 435/235, 325, 435/378, 377, 366; 424/93.1, 93.21, 93.7

[56] References Cited

U.S. PATENT DOCUMENTS

| | | | |
|---|---|---|---|
| 4,352,883 | 10/1982 | Lim | 435/178 |
| 4,609,551 | 9/1986 | Caplan et al. | 424/95 |
| 4,846,835 | 7/1989 | Grande | 623/11 |
| 4,963,489 | 10/1990 | Naughton et al. | 435/240.1 |
| 5,041,138 | 8/1991 | Vacanti et al. | 623/16 |
| 5,197,985 | 3/1993 | Caplan et al. | 623/16 |
| 5,226,914 | 7/1993 | Caplan et al. | 623/16 |
| 5,486,359 | 1/1996 | Caplan et al. | 424/93.7 |

FOREIGN PATENT DOCUMENTS

| | | |
|---|---|---|
| 2 137 209 | 10/1984 | United Kingdom . |
| WO 90/12603 | 11/1990 | WIPO . |
| WO 95/33821 | 12/1995 | WIPO . |
| WO 96/28539 | 9/1996 | WIPO . |

OTHER PUBLICATIONS

Sandell et al. Alternatively spliced type II procollagen mRNAs define distinct populations of cells during vertebral development: differential expression of the amino–propeptide. Journal of Cell Biology, vol. 114, No. 6, pp. 1307–1319, Sep. 1991.

Elima et al. Expression of mRNAs for collagens and other matrix components in dedifferentiating and redifferentiating human chondrocytes in culture. FEBS letters, vol. 258, No. 2, pp. 195–198, 1989.

Grande, D.A. et al., 1995, "Repair of Articular Cartilage Defects Using Mesenchymal Stem Cells", Tissue Engineering 1: 345–353.

Corvetti and Cameron–Curry, 1986, "Immunohistochemical and Ultrastructural Study of Two Human Loose Mucoid Connective Tissues", Arch. Ital. Anat. Embriol. 91(1):9–19 and Biol. Abstr. 83(5):111 (Abstr. No. 40785, 1987).

Naughton et al., 1997, "Cells Isolated from Wharton's Jelly of the Human Umbilical Cord Develop a Cartilage Phenotype when Treated with TGF$_\beta$ In Vitro", FASEB J. 11(3):A19 (Abstr. No. 108).

Adams, J. et al., 1995, "The c–myc Oncogene Driven by Immunboglobulin Enhancers Inuces Lymphoid Malignancy in Transgenic Mice", Nature 318:533–538.

Alexander et al., 1987, "Expression of the c–myc Oncogene under Control of an Immunoglobulin Enhancer in E$\mu$–myc Transgenic Mice", Mol. Cell Biol. 7:1436–1444.

Alexandrow and Moses, 1995, "Transforming Growth Factor $\beta$ and Cell Cycle Regulation", Cancer Res. 55:1452–1457.

Allcock et al., 1977, "Synthesis of Poly[(amino acid alkyl ester) phosphazenes]$^{1-3}$", Macromolecules 10:824–830.

Assoian, R. et al., 1983, "Transforming Growth Factor–$\beta$ in Human Platelets", J. of Biol. Chem. 258:7155–7160.

Barnard, J.et al., 1990, "The Cell Biology of Transforming Growth Factor $\beta$", Biochem. Biophys. Acta 1032:79–87.

Beck, et al., 1991, "In Vivo Induction of Bone by Recombinant Human Transforming Growth Factor $\beta_1$", J. Bone Mineral Res. 6:961–968.

Burch, W. et al., 1985, "Homologous and Heterologous Growth Hormones Fail to Stimulate Avian Cartilage Growth in Vitro", J. Clin. Endocrinol. Metab. 60:747–750.

Campbell, I. et al., 1991, "Human Articular Cartilage and Chondrocytes Produce Hemopoietic Colony–Stimulating Factors in Culture in Response to IL–1", J. Immunology 147:1238–1246.

Caplan, A., 1991, "Mesenchymal Stem Cells", J. of Orthopaedic Res. 9:641–650.

Cate, R. et al., 1986, "Isolation of the Bovine and Human Genes for Mullerian Inhibiting Substance and Expression of the Human Gene in Animal Cells", Cell 45:685–698.

Centrella, M. et al., 1987, "Transforming Growth Factor $\beta$ is a Bifunctional Regulator of Replication and Collagen Synthesis in Osteoblast–enriched Cell Cultures from Fetal Rat Bone", J. Biol. Chem. 262:2869–2874.

Coffey, R. et al., 1988, "Growth Modulation of Mouse Keratinocytes by Transforming Growth Factors", Cancer Res. 48:1596–1602.

Cormack, D., 1987, "Ham's Histology", J.B. Lippincott Company, pp. 266–272.

DeMartin et al., 1987, "Complementary DNA for Human Glioblastoma–derived T Cell Suppressor Factor, a Novel Member of the Transforming Growth Factor–$\beta$ Gene Family", EMBO J. 6:3676–3677.

Derynck, R. et al., 1988, "A New Type of Transforming Growth Factor–$\beta$TGF–$\beta$3", EMBO J. 7:3737–3743.

(List continued on next page.)

*Primary Examiner*—Brian R. Stanton
*Assistant Examiner*—Deborah J. R. Clark
*Attorney, Agent, or Firm*—Pennie & Edmonds llp

[57] ABSTRACT

The invention relates to the isolation and use of pre-chondrocytes from the umbilical cord, specifically from Wharton's jelly, that give rise to chondrocytes which produce cartilage. The isolated pre-chondrocytes, or the chondrocytes to which they give rise, can be mitotically expanded in culture and used in the production of new cartilage tissue for therapeutic use. "Banks" of pre-chondrocytes or chondrocytes can be stored frozen, and thawed and used to produce new cartilage tissue as needed.

6 Claims, 11 Drawing Sheets

OTHER PUBLICATIONS

Derynck, R. et al., 1985, "Human Transforming Growth Factor–β Complementary DNA Sequence and Expression in Normal and Transformed Cells", Nature 316:701–705.

Domb, A., et al., 1992, "Degradable Polymers for Site Specific Drug Delivery," 3:279–292.

Freshney, R.I., 1987, "Culture of Animal Cells", Alan R. Liss, Inc., New York, Chapt. 14, p. 187.

Galera, P. et al., 1992, "Transforming Growth Factor–β1 (TGF–β1) Up–Regulation of Collagen Type II in Primary Cultures of Rabbit Articular Chondrocytes (RAC) Involves Increased mRNA Levels without Affecting mRNA Stability and Procollagen Processing", J. Cell Physio. 153:596–606.

Gentry, L. et al., 1987, "Type 1 Transforming Growth Factor Beta: Amplified Expression and Secretion of Mature and Precursor Polypeptides in Chinese Hamster Ovary Cells", Mol. and Cell. Biol. 7:3418–3427.

Gill, P. et al., 1993, "Wharton's Jelly in the Umbilical Cord", J. of Reprod. Med. 38:611–614.

Goey, H. et al., 1989, "Inhibition of Early Murine Hemopoietic Progenitor Cell Proliferation after In Vivo Locoregional Administration of Transforming Growth Factor–β1", J. of Immunol. 143:877–880.

Goldkorn et al., 1992, "Transforming Growth Factor β Modulates Phosphorylation of the Epidermal Growth Factor Receptor and Proliferation of A431 Cells," Cell Growth and Diff. 3:101–109.

Goldring et al., 1988, "Interleukin 1 Suppresses Expression of Cartilage–specific Types II and IX Collagens and Increases Types I and III Collagens in Human Chondrocytes", J. Clin. Invest. 82:2026–2037.

Grosschedl, R. et al., 1984, "Introduction of a $\mu$ Immunoglobulin Gene into the Mouse Germ Line: Specific Expression in Lymphoid Cells and Synthesis of Functonal Antibody", Cell 38:647–658.

Hamerman, D. et al., 1986, "A Cartilage–Derived Growth Factor Enhances Hyaluronate Synthesis and Diminishes Sulfated Glycosaminoglycan Synthesis in Chondrocytes", J. Cell. Physio. 127:317–322.

Hanahan, D., 1985, "Heritable Formation of Pancreatic β–Cell Tumors in Transgenic Mice Expressing Recombinant Insulin/Simian Virus 40 Oncogenes", Nature 315:115–122.

Hanks, S. et al., 1988, "Amino Acid Sequence of the BSC–1 Cell Growth Inhibitor (Polyergin) Deduced from the Nucleotide Sequence of the cDNA", PNAS USA 85:79–82.

Hattersley et al., 1995, J. Bone and Mineral Res. 10:S163.

Horton, W. et al., 1989, "Transforming Growth Factor–Beta and Fibroblast Growth Factor Act Synergistically to Inhibit Collagen II Synthesis through a Mechanism Involving Regulatory DNA Sequences", J. Cell. Physio. 141:8–15.

Ignotz and Massague, 1986, "Transforming Growth Factor–β Stimulates the Expression of Fibronectin and Collagen and Their Incorporation into the Extracellular Matrix", J. Biol. Chem. 26:4337–4345.

Ikebe, T. et al., 1988, "Effects of Human Recombinant Tumor Necrosis Factor–α and Interleukin 1 on the Synthesis of Glycosaminoglycan and DNA in Cultured Rat Costal Chondrocytes", J. Immunol. 140:827–831.

Ikeda, T. et al., 1987, "Human transforming Growth Factor Type β2: Production by a Prostatic Adenocarcinoma Cell Line, Purification, and Initial Characterization", Biochemistry 26:2406–2410.

Inada, M. et al., 1996, "Bone Morphogenetic Protein 12 and –13 Inhibit Terminal Differentiation of Myoblasts, but Do Not Induce Their Differentiation into Osteoblasts", Biochem. and Biophys. Res. Comm. 222:317–322.

Jackson, R.W., 1983, "Current Concepts Review Arthroscopic Surgery", J. of Bone and Joint Surgery 65–A:416–420.

Jakowlew et al., 1988, "Complementary Deoxyribonucleic Acid Cloning of a Novel Transforming Growth Factor–β Messenger Ribonucleic Acid from Chick Embryo Chondrocytes", Mol. Endocrinol. 2:747–755.

Jakowlew et al., 1988, "A Novel Low Molecular Weight Ribonucleic Acid (RNA) Related to Transforming Growth Factor α Messenger RNA", Mol. Endocrinol. 2:1056–1063.

Joyce, M. et al., 1990, "Transforming Growth Factor–β and the Initiation of Chondrogenesis and Osteogenesis in the Rat Femur", J. Cell Biol. 110:2195–2207.

Kasid, A. et al., 1988, "Effects of Transforming Growth Factor–β on Human Lymphokine–activated Killer Cell Precursors", J. Immunol. 141:690–698.

Kehrl, J. et al., 1986, "Production of Transforming Growth Factor β by Human T Lymphocytes and its Potential Role in the Regulation of T Cell Growth", J. Exp. Med 163:1037–1050.

Kondaiah, P. et al., 1990, "Identification of a Novel Transforming Growth Factor–β (TGF–β5) mRNA in *Xenoous laevis*", J. Biol. Chem. 265:1089–1093.

Kuruvilla, A.P. et al., 1991, "Protective Effect of Transforming Growth Factor $\beta_1$ on Experimental Autoimmune Diseases in Mice", PNAS USA 88:2918–2921.

Lee, S., 1990, "Identification of a Novel Member (GDF–1) of the Transforming Growth Factor–β Superfamily", Mol. Endocrinol. 4:1034–1040.

Lefebvre, V. et al., 1990, "Modulation by Interleukin 1 and Tumor Necrosis Factor α of Production of Collagenase, Tissue Inhibitor of Metalloproteinases and Collagen Types in Differentiated and Dedifferentiated Articular Chondrocytes", Biophys. Acta 1052:366–372.

Lefer, A. et al., 1993, "Mechanism of the Cardioprotective Effect of Transforming Growth Factor $\beta_1$ in Feline Myocardial Ischemia and Reperfusion", PNAS USA 90:1018–1022.

Lefer, A. et al., 1990, "Mediation of Cardioprotection by Transforming Growth Factor–β", Science 249:61–64.

Lindahl, A. et al., 1987, "Effects of Growth Hormone and Insulin–like Growth Factor–I on Colony Formation of Rabbit Epiphyseal Chondrocytes at Different Stages of Maturation", J. Endocr. 115:263–271.

MacDonald, R., 1987, "Expression of the Pancreatic Elastase I Gene in Transgenic Mice", Hepatology 7:425–515.

Mackie and Trechsel, 1990, "Stimulation of Bone Formation In Vivo by Transforming Growth Factor—Beta: Remodeling of Woven Bone and Lack of Inhibition by Indomethacin", Bone 11:295–300.

Madisen, L. et al., 1988, "Transforming Growth Factor–β2: cDNA Cloning and Sequence Analysis", DNA 7:1–8.

Makower, A.M. et al., 1989, "Effects of IGF–I, rGH, FGF, EGF and NCS on DNA–Synthesis, Cell Proliferation and Morphology of Chondrocytes Isolated from Rat Rib Growth Cartilage", Cell Biol. Internat'l Reports 13:259–270.

Malemud, C. et al., 1991, "Enhanced Sulfated–Proteoglycan Core Protein Synthesis by Incubation of Rabbit Chondrocytes with Recombinant Transforming Growth Factor–$\beta_1$", J. Cell Physio. 149:152–159.

Maor, G. et al., 1989, "Human Growth Hormone Enhances Chondrogenesis and Osteogenesis in a Tissue Culture System of Chondroprogenitor Cells", Endocrinology 125:1239–1245.

Marcelli, C. et al., 1990, "In Vivo Effects of Human Recombinant Transforming Growth Factor β on Bone Turnover in Normal Mice", J. Bone Mineral Res. 5:1087–1096.

Marquardt, H. et al., 1987, "Complete Amino Acid Sequence of Human Transforming Growth Factor Type β2", J. Biol. Chem. 262:12127–12131.

Mason, et al., 1986, "the Hypogonadal Mouse: Reproductive Functions Restored by Gene Therapy," Science 234:1372–1378.

Mason, A. et al., 1985, "Complementary DNA Sequences of Ovarian Follicular Fluid Inhibin Show Precursor Structure and Homology with Transforming Growth Factor–β", Nature 318:659–663.

Massague, J., 1990, "The Transforming Growth Factor–β Family", Annu. Rev. Cell Biol. 6:597–641.

McCurry, K. et al., 1995, "Human Complement Regulatory Proteins Protect Swine–to–Primate Cardiac Xenografts from Humoral Injury", Nature Med. 1:423–427.

McElreavey, K. et al., 1991, "Isolation, Culture and Characterization of Fibroblast–like Cells Derived from the Wharton's Jelly Portion of Human Umbilical Cord", BCSTB5 9:29S (Abstract).

McPherron and Lee, 1993, "GDF–3 and GDF–9: Two New Members of the Transforming Growth Factor–β Superfamily Containing a Novel Pattern of Cysteines", J. Biol. Chem. 268:3444–3449.

McQuillan, D. et al., 1986, "Stimulation of Proteoglycan Biosynthesis by Serum and Insulin–like Growth Factor–I in Cultured Bovine Articular Cartilage", Biochem. J. 240:423–430.

Meyer, F. et al., 1983, "Evidence for a Mechanical Coupling of Glycoprotein Microfibrils with Collagen Fibrils in Wharton's Jelly", Biochimica et Biophysica Acta 755:376–387.

Mombaerts, P. et al., 1991, "Creation of a Large Genomic Deletion at the T–cell Antigen Receptor β–Subunit Locus in Mouse Embryonic Stem Cells by Gene Targeting", PNAS USA 88:3084–3087.

Moses, H. et al., 1981, "Transforming Growth Factor Production by Chemically Transformed Cells", Cancer Res. 41:2842–2848.

Mustoe, T. et al., 1987, "Accelerated Healing of Incisional Wounds in Rats Induced by Transforming Growth Factor–β", Science 237:1333–1335.

Naughton, B. et al., 1987, "Hematopoiesis on Nylon Mesh Templates", J. Med. 18:219–250.

Noda and Camilliere, 1989, "In Vivo Stimulation of Bone Formation by Transforming Growth Factor–β", Endocrinology 124:2991–2994.

Nugent and Edelman, 1992, "Transforming Growth Factor β1 Stimulates the Production of Basic Fibroblast Growth Factor Binding Proteoglycans in Balb/c3T3 Cells", J. Biol. Chem. 267:21256–21264.

Oberhammer, F. et al., 1992, Induction of Apoptosis in Cultured Hepatocytes and in Regressing Liver by Transforming Growth Factor β1, PNAS USA 89:5408–5412.

Ornitz, D.M. et al., 1986, "Elastase I Promoter Directs Expression of Human Growth Hormone and SV40 T Antigen Genes to Pancreatic Acinar Cells in Transgenic Mice", Cold Spring Harb. Symp. Quant. Biol. 50:399–409.

Osborn, K. et al., 1989, "Growth Factor Stimulation of Adult Articular Cartilage", J. Ortho. Res. 7:35–42.

Ozkaynak, E. et al., 1992, "Osteogenic Protein–2", J. Biol. Chem. 267:25220–25227.

Ozkaynak, E. et al., 1990, "OP–1 cDNA Encodes an Osteogenic Protein in the TGF–β Family", EMBO J. 7:2085–2093.

Pietenpol, J. et al., 1990, "TGF–β1 Inhibition of c–myc Transcription and Growth in Keratinocytes is Abrogated by Viral Transforming Proteins with pRB Binding Domains", Cell 61:777–785.

Pieter, A. et al., 1982, "Effect of Purified Growth Factors on Rabbit Articular Chondrocytes in Monolayer Culture", Arthritis and Rheumatism 25:1228–1238.

Phillips, C. et al., 1994, "Effects of Ascorbic Acid on Proliferation and Collagen Synthesis in Relation to the Donor Age of Human Dermal Fibroblasts", Soc. Inv. Derm. 103–2:228–232.

Ranchalis, J. et al., 1987, "Bone–derived and Recombinant Transforming Growth Factor β's are Potent Inhibitors of Tumor Cell Growth", Biophys. Res. Commun. 148:783–789.

Readhead, C. et al., 1987, "Expression of a Myelin Basic protein Gene in Transgenic Shiverer Mice: Correction of the Dysmyelinating Phenotype", Cell 48:703–712.

Roberts and Sporn, 1990, in: M.B. Sporn and A.B. Roberts (eds.), Peptide Growth Factors and Their Receptors I, Springer–Verlag, Berlin, pp. 419–472.

Roberts, A. et al., 1985,, "Type β Transforming Growth Factor: A Bifunctioinal Regulator of Cellular Growth", PNAS USA 82:119–123.

Roberts, A. et al., 1981, "New Class of Transforming Growth Factors Potentiated by Epidermal Growth Factor: Isolation from Non–Neoplastic Tissues", PNAS USA 78:5339–5343.

Robinson, S. et al., 1993, "TGFβ Suppresses Casein Synthesis in Mouse Mammary Explants and May Play a Role in Controlling Milk Levels during Pregnancy", J. Cell Biol. 120:245–251.

Rosen, D. et al., 1988, "Transforming Growth Factor–Beta Modulates the Expression of Osteoblast and Chrondroblast Phenotypes In Vitro", J. Cell. Physio. 134:337–346.

Rotello, R. et al., 1991, "Coordinated Regulation of Apoptosis and Cell Proliferation by Transforming Growth Factor β1 in Cultured Uterine Epithelial Cells", PNAS USA 88:3412–3415.

Saklatvala, J., 1986, "Tumour Necrosis Factor α Stimulates Resorption and Inhibits Synthesis of Proteoglycan in Cartilage", Nature 322:547–549.

Selden, R. et al., 1987, "Implantation of Genetically Engineered Fibroblasts into Mice: Implications for Gene Therapy", Science 236:714–718.

Seyedin, S. et al., 1987, "Cartilage–inducing Factor–B Is a Unique Protein Structurally and Functionally Related to Transforming Growth Factor–β", J. Biol. Chem. 262:1946–1949.

Seyedin, S. et al., 1986, "Cartilage–inducing Factor–A", J. Biol. Chem. 261:5693–5695.

Shani, M., 1985, "Tissue–Specific Expression of Rat Myosin Light–Chain 2 Gene in Transgenic Mice", Nature 314:283–286.

Sharples, K. et al., 1987, "Cloning and Sequence Analysis of Simian Transforming Growth Factor–β cDNA", EMBO J. 6:239–244.

Swift, G. et al., 1984, "Tissue–Specific Expression of the Rat Pancreatic Elastase I Gene in Transgenic Mice", Cell 38:639–646.

Takechi, K. et al., 1993, "Ultrastructural and Immunohistochemical Studies of Wharton's Jelly Umbilical Cord Cells", Placenta 14:235–245.

Tiku, M. et al., 1990, "Production of Hydrogen Peroxide by Rabbit Articular Chondrocytes", J. Immunol. 145:690–696.

Tucker, R. et al., 1984, "Specific Binding to Cultured Cells of $^{125}$I–labeled type β Transforming Growth Factor from Human Platelets", PNAS USA 81:6757–6761.

Tyler, J. et al., 1988, "Synthesis of Type II collagen is Decreased in Cartilage Cultured with Interleukin 1 while the Rate of Intracellular Degradation Remains Unchanged", Coll. Relat. Res. 82:393–405.

Tyler, J., 1985, "Chondrocyte–mediated Depletion of Articular Cartilage Proteoglycans in vitro", Biochem. J. 225:493–507.

Tyler, J., 1985, "Articular Cartilage Cultured with Catabolin (Pig Interleukin 1) Synthesizes a Decreased Number of Normal Proteoglycan Molecules", Biochem. J. 227:869–878.

Whitson and Itakura, 1992, "TGF–$β_1$ Inhibits DNA Synthesis and Phosphorylation of the Retinoblastoma Gene Product in a Rat Liver Epithelial Cell Line", J. Cell Biochem. 48:30.

Wozney, J. et al., 1988, "Novel Regulators of Bone Formation: Molecular Clones and Activities", Science 242:1528–1534.

Yaron, I. et al., 1989, "Some Recombinant Human Cytokines Stimulate Glycosaminoglycan Synthesis in Human Synovial Fibroblast Cultures and Inhibit it in Human Articular Cartilage Cultures", Arthritis and Rheumatism 32:173–180.

Zhou, X. et al., 1993, "Nodal is a Novel TGF–β–like Gene Expressed in the Mouse Node during Gastrulation", Nature 361:543–547.

PRODUCTION OF CARTILAGE TISSUE USING CELLS ISOLATED FROM WHARTON'S JELLY

1. INTRODUCTION

The invention relates to compositions and methods for the production of cartilage tissue. More specifically, the invention relates to methods for the isolation of pre-chondrocytes from umbilical cord sources such as Wharton's jelly, which cells give rise to chondrocytes that produce cartilage tissue. The isolated pre-chondrocytes, or the chondrocytes to which they give rise, can be mitotically expanded in culture and induced to form cartilage tissue with a wide range of therapeutic uses. The pre-chondrocytes of the invention, or the chondrocytes produced therefrom, can be cryopreserved and stored frozen to form "banks" of cells which can be thawed and used to produce new cartilage tissue as needed. This is particularly advantageous when used for production of human cartilage tissue.

The invention is demonstrated by way of examples describing the isolation from Wharton's jelly of pre-chondrocytes, their mitotic expansion, and seeding onto a three-dimensional framework on which they were induced to form cartilage tissue.

2. BACKGROUND OF THE INVENTION

2.1. Uses for Replacement Cartilage Tissue

Cartilage may be damaged by disease, such as rheumatoid or osteoarthritis, or by trauma, which can lead to serious physical deformity and debilitation. As human articular cartilage ages, its sheer compressive and tensile properties change. The superficial zone of the knee articular cartilage exhibits an increase in tensile strength up to the third decade of life, after which tensile strength decreases markedly with age as detectable damage to type II collagen occurs at the articular surface. Deep zone cartilage also exhibits a progressive decrease in tensile strength with increasing age, although collagen content does not decrease. These observations indicate that there are changes in mechanical and, hence, structural organization of cartilage with aging that, if sufficiently developed, can predispose cartilage to traumatic damage. In osteoarthritic cartilage there is excessive damage to type II collagen, resulting in crimping of collagen fibrils. In rheumatoid arthritis, the combined actions of free radicals and proteinases released from polymorpholeukocytes cause much of the damage seen at the articular surface. (Tiku et al., 1990, J. Immunol. 145:690–696). Induction of cartilage matrix degradation and proteinases by chondrocytes is probably induced primarily by interleukin-1 (IL-1) or tumor necrosis factor-$\alpha$ (TNF-$\alpha$) (Tyler, 1985, Biochem. J. 225:493–507).

A source of replacement cartilage tissue would thus be useful in most cases of cartilage disease or trauma.

2.2. Current Therapies for Loss of Cartilage

The current therapy for loss of cartilage tissue is replacement with a prosthetic material such as, for example, silicone for cosmetic repairs, or metal alloys for joint refinement. Placement of prosthetic devices, however, is usually associated with loss of underlying tissue and bone without recovery of the full function allowed by the original cartilage tissue. Serious long-term complications associated with the presence of a permanent foreign body can include infection, erosion and instability.

Use of sterilized bone or bone powder with surgical steel seeded with bone cells which were eventually implanted have been largely unsuccessful because of the non-degradable nature of the cell support. U.S. Pat. No. 4,609,551 to Caplan, issued Sep. 2, 1986, discloses that fibroblasts are exposed in vitro for a minimum of three days to a soluble bone protein capable of stimulating in vitro and/or in vivo a chondrogenic response. The activated fibroblasts are then transferred in vivo by combining them with a biodegradable matrix, or by intra-articular injection or attachment to allografts and prosthetic devices. The disadvantage of this method is that chondrogenesis is not allowed to develop in the short-term cultures and there is an unduly heavy reliance on the exposed fibroblasts at the implant site for cartilage synthesis.

Alternatively, chondrocytes have been isolated, mitotically expanded in vitro, and either directly administered to the site of damage to produce new cartilage tissue in vivo, or cultured to produce new cartilage tissue in vitro which is then grafted to the site of tissue damage. For example, U.S. Pat. No. 4,846,835 to Grande, issued Jul. 11, 1989, discloses the seeding of autologous chondrocytes onto a three dimensional collagen matrix which is then inserted in vivo at the site of an articular cartilage lesion and fixed in place using a sutured periosteal flap. U.S. Pat. No. 5,041,138 to Vacanti et al., issued Aug. 20, 1991, discloses the in vitro growth of cartilaginous structures by seeding chondrocytes onto a three dimensional biodegradable matrix for subsequent implantation, or, alternatively, proliferating free chondrocytes in vitro, which are then administered directly to the site of damage.

2.3. Sources of Cartilage-Producing Cells

Chondrocytes can be obtained from normal mature cartilage tissue. For example, both U.S. Pat. No. 4,846,835 to Grande, supra, and U.S. Pat. No. 5,041,138 to Vacanti et al., supra, disclose the obtention of chondrocytes by digesting articular cartilage in a collagenase solution, followed by mitotic expansion of the chondrocytes in an in vitro culture medium prior to implantation.

Once a mitotically expanded population of chondrocytes is obtained, the cells can be implanted either back into the same subject from which their parent cells were originally derived (autologous implantation), or into a different subject (heterologous implantation). In addition, heterologous implantation may utilize chondrocytes obtained from a related or unrelated individual of the same species (allogeneic), or from a different species (xenogeneic). Alternatively, chondrocytes may be obtained from an established, long-term cell line that is either allogeneic or xenogeneic.

Autologous implantation requires that chondrocytes or pre-chondrocytes are harvested from the patient and then mitotically expanded to sufficient number or density to allow for an effective implant. The amount of time required for sufficient expansion to an effective cell number or density, however, may preclude the effective use of an autologous culture since some repairs to cartilage should be carried out immediately or within a short time after a traumatic injury occurs. Another limitation is the mitotic potential of the cells, since there is a limitation to the number of times the cells can be expanded, the ultimate quantity of cells produced for therapy may be limited. In addition, where a severe, debilitating joint disorder causes general degradation of cartilage tissue throughout a patient's body, there may be very little unaffected cartilage tissue available from which to initiate a chondrocyte culture.

Use of a heterologous culture poses its own potential problems, including the possibility of an immune reaction and potential rejection of the newly-formed and engrafted cartilage tissue. In addition, heterologous implantation risks the transmission to the subject of any infectious agent(s) present in the tissue or cell line.

Mesenchymal cells are a potential alternative source of cartilage-producing cells. Mesenchymal cells are generally recognized as multipotential cells which are capable of dividing many times to produce progeny cells that can eventually give rise to skeletal tissues, including cartilage, bone, tendon, ligament, marrow stroma and connective tissue. By definition, these mesenchymal cells are generally considered to not be governed by, or are not limited to, a fixed number of mitotic divisions (Caplan, 1991, J. Orthopaed. Res. 9:641–650). U.S. Pat. Nos. 5,197,985 and 5,226,914 to Caplan et al., issued Mar. 30, 1993 and Jul. 13, 1993, respectively, disclose a process for isolating and replicating human bone marrow-derived mesenchymal cells in culture, and activating them so that they differentiate either into bone or, purportedly, into cartilage. Likewise, U.S. Pat. No. 5,486,359 to Caplan et al., issued Jan. 23, 1996, discloses human mesenchymal stem cells and monoclonal antibodies to these cells. Again, culturing the cells so that they differentiate into various tissue types is disclosed. Note, however, that only bone formation was exemplified within the above Caplan patents. In fact, no data was presented showing that such cells can, in fact, be utilized to produce chondrocytes or that cartilage tissue could be produced by the disclosed process. Furthermore, unless the mesenchymal cells are autologous, their use fails to overcome the potential problems of immune rejection or transfer of infectious agents, as discussed supra. Moreover, the Caplan patents do not disclose Wharton's jelly of the umbilical cord as a source of cells capable of producing cartilage.

Thus, methods for producing new cartilage tissue for use in the therapeutic treatment of disease or trauma would benefit from a more readily available source of chondrocytes that do not risk triggering an immune response, and that do not carry any infectious agents.

2.4. Role of Growth Factors and Hormones in Cartilage Formation

Growth factors have paracrine or autocrine effects on cell metabolism and can retard or enhance chondrocyte division, matrix synthesis, and degradation, as described below.

2.4.1. Transforming Growth Factor-β

Transforming growth factor-β ("TGF-β") refers to a growing family of related dimeric proteins which regulate the growth and differentiation of many cell types (Barnard et al., 1990, Biochem. Biophys. Acta. 1032:79–87; Massague, 1990, Annu. Rev. Cell. Biol. 6:597–619; Roberts and Sporn, 1990, in: M. B. Sporn and A. B. Roberts (eds.), *Peptide Growth Factors and Their Receptors I*, Springer-Verlag, Berlin, pp. 419–472). Members of this family include TGF-β1 (Derynck et al., 1985, Nature 316:701–705; Moses et al., 1981, Cancer Res. 41:2842–2848; Roberts et al., 1981, Proc. Natl. Acad. Sci. USA 78:5339–5343; Sharples et al., 1987, DNA 6:239–244); TGF-β2 (DeMartin et al., 1987, EMBO J. 6:3676–3677; Hanks et al., 1988, Proc. Natl. Acad. Sci. USA 85:79–82; Ikeda et al., 1987, Biochemistry 26:2406–2410; Madisen et al., 1988, DNA 7:1–8; Marquardt et al., 1987, Biol. Chem. 262:12127–12131; Seyedin et al., 1987, J. Biol. Chem. 262:1946–1949); TGF-β3 (Derynck et al., 1988, EMBO J. 7:3737–3743; Jakowlew et al., 1988, Endocrinol. 2:747–755); TGF-β4 (Jakowlew et al., 1988, Mol. Endocrinol. 2:1064–1069); TGF-β5 (Kondaiah et al., 1990, J. Biol. Chem. 265:1089–1093); and the more distantly related Mullerian inhibitory substance (Cate et al., 1986, Cell. 45:685–698); the inhibins (Mason et al., 1985, Nature 318:659–663); the bone morphogenetic proteins (Wozney et al., 1988, Science 242:1528–1534); and OP-1 (Özkaynak et al., 1990, EMBO J. 9:2085–2093). Newly discovered members include OP-2 (Özkaynak et al., 1992, J. Biol. Chem. 267:25220–25227); GDF-1 (Lee, 1990, Mol. Endocrinol. 4:1034–1040); GDF-3 and GDF-9 (McPherron and Lee, 1993, J. Biol. Chem. 268:3444–3449); and Nodal (Zhou et al., 1993, Nature 361:543–546).

TGF-β was first characterized for its effects on cell proliferation. It both stimulated the anchorage-independent growth of rat kidney fibroblasts (Roberts et al., 1981, supra), and inhibited the growth of monkey kidney cells (Tucker et al., 1984, Proc. Natl. Acad. Sci. USA 81:6757–6761). TGF-β has since been shown to have many diverse biological effects, e.g., it stimulates bone formation (Noda and Camilliere, 1989, Endocrinol. 124:2991–2995; Joyce et al., 1990, J. Cell. Biol. 110:2195–2207; Marcelli et al., 1990, J. Bone Mineral Res. 5:1087–1096; Beck et al., 1991, J. Bone Mineral Res. 6:961; Mackie and Trechsel, 1990, J. Cell. Biol. 110, 2195–2207); induces rat muscle cells to produce cartilage-specific macromolecules (Seyedin et al., 1984, J. Biol. Chem. 261:5693–5695; Seyedin et al., 1986, J. Biol. Chem. 261:5693–5695; and Seyedin et al., 1987, J. Biol. Chem. 262:1946–1949); inhibits the growth of early hematopoietic progenitor cells (Goey et al., 1989, J. Immunol. 143:877–880), T cells (Kehrl et al., 1986, J. Exp. Med. 163:10375–1050), B cells (Kasid et al., 1988, J. Immunol. 141:690–698), mouse keratinocytes (Pietenpol et al., 1990, Cell 61:777–785; Coffey et al., 1988, Cancer Res. 48:1596–1602), and several human cancer cell lines (Roberts et al., 1985, Proc. Natl. Acad. Sci. USA 82:119–123; Ranchalis et al., 1987, Biophys. Res. Commun. 148:783–789). TGF-β increases the synthesis and secretion of collagen and fibronectin (Ignotz and Massague, 1986, J. Biol. Chem. 261:4337–4345; Centrella et al., 1987, J. Biol. Chem. 262:2869–2874; Malemud et al., 1991, J. Cell Physio. 149:152–159; Galéra et al., 1992, J. Cell Physio. 153:596–606; Phillips et al., 1994, Soc. Inv. Derm. 1032:228–232); accelerates healing of incisional wounds (Mustoe et al., 1987, Science 237:1333–1335); suppresses casein synthesis in mouse mammary explants (Robinson et al., 1993, J. Cell. Biol. 120:245–251); inhibits DNA synthesis and phosphorylation of pRb in rat liver epithelial cells (Whitson and Itakura, 1992, J. Cell. Biochem. 48:305–315); stimulates the production of BFGF binding proteoglycans (Nugent and Edelman, 1992, J. Biol. Chem. 267:21256–21264); modulates phosphorylation of the EGF receptor and proliferation of epidermoid carcinoma cells (Goldkorn and Mendelsohn, 1992, Cell Growth and Differentiation, 3:101–109); and can lead to apoptosis in uterine epithelial cells (Rotello et al., 1991, Proc. Natl. Acad. Sci. USA 88:3412–3415), cultured hepatocytes and regressing liver (Oberhammer et al., 1992, Proc. Natl. Acad. Sci. USA 89:5408–5412). TGF-β can mediate cardio-protection against reperfusion injury by inhibiting neutrophil adherence to endothelium (Lefer et al., 1990, Science 249:61–64; Lefer et al., 1993, Proc. Natl. Acad. Sci. USA 90:1018–1022); and it protects against experimental autoimmune diseases in mice (Kuruvilla et al., 1991, Proc. Natl. Acad. Sci. USA 88:2918–2921).

In contrast to the foregoing reports of the ability of TGF-β to induce the production of cartilage-specific macromolecules in muscle cells and chondrocytes, TGF-β was found to act synergistically with fibroblast growth factor to inhibit the synthesis of collagen type II by chicken sternal chondrocytes (Horton et al., 1989, J. Cell Physio. 141:8–15); and TGF-β inhibited production of type II collagen in rat chondrocytes (Rosen et al., 1988, J. Cell Physio. 134:337–346). In fact, TGF-β has emerged as the prototypical inhibitor of the proliferation of most normal cell types in vitro as well as in vivo, exhibiting a remarkable diversity of biological activity (Alexandrow and Moses, 1995, Cancer Res. 55:1452–1457).

TGF-β1 has been purified from human and porcine blood platelets (Assoian et al., 1983, J. Biol. Chem. 258:7155–7160), and recombinant TGF-β1 is currently available (Gentry et al., 1988, Mol. Cell. Biol. 7:3418–3427).

2.4.2. Insulin-Like Growth Factors I and II

Insulin alone is much less potent than insulin-like growth factor (IGF-I) in stimulating collagen matrix synthesis. Insulin, however, enhances proteoglycan synthesis in the presence of a low concentration of serum (1%). IGF-I, previously designated somatomedin c, is a potent inducer of collagen and proteoglycan synthesis in vitro. (Lindahl et al., 1987, J. Endocrinol. 115:263–271; Markower et al., 1989, Cell. Biol. Int. Rep. 13:259–270).

Insulin-like growth factor-II (IGF-II) stimulates DNA and RNA synthesis and is more potent than IGF-I in stimulating clonal growth in fetal cells, whereas IGF-I is more effective on adult chondrocytes. IGF-II can stimulate proteoglycan synthesis, but, like insulin, is much less effective than IGF-I (McQuillan et al., 1986, Biochem. J. 240:423–430).

2.4.3. Growth Hormone

Parenteral administration of growth hormone (GH) can stimulate localized growth plate development in vivo. Hypophysectomy leads to disappearance of IGF-I in growth plate chondrocytes, indicating a cessation of synthesis. On the other hand, systemic or local treatment with GH results in the appearance of IGF-I. Reports of direct stimulatory effects of GH on cell growth in vitro (Maro et al., 1989, Endocrinol. 125:1239–1445) conflict with reports that it has no effect (Burch et al., 1985, J. Clin. Endocrinol. Metab. 60:747–750).

2.4.4. Other Growth Factors

Epidermal growth factor (EGF) alone has no effect on chondrocyte proliferation. Together with insulin, EGF synergistically stimulates proteoglycan synthesis and induces proliferation of chondrocytes. (Osborn et al., 1989, J. Orthop. Res. 7:35–42). Basic fibroblast growth factor (bFGF) inhibits proteoglycan synthesis in fetal articular cartilage (Hamerman et al., 1986, J. Cell. Physiol. 127:317–322), but appears to function additively with IGF-I in adult articular cartilage and stimulates proteoglycan synthesis (Osborn, K. D., et al., 1989, J. Orthop. Res. 7:35–42). Platelet-derived growth factor (PDGF) also enhances proteoglycan synthesis (Prins et al., 1982, Arthritis Rheum. 25:1228–1238). Certain bone morphogenic proteins (BMPs) stimulate chondrogenesis and promote cartilage production (Inada et al., 1996, Biochem. and Biophys. Res. Comm. 222(2):317–322; Hattersley et al., 1995, J. Bone and Mineral Res. 10(1):PS163).

3. SUMMARY OF THE INVENTION

The present invention relates to compositions and methods for the production of cartilage tissue in vitro or in vivo, which can be used for a wide variety of purposes. In accordance with the invention, chondrocyte progenitor cells, or "pre-chondrocytes," are isolated from umbilical cord sources, most preferably from Wharton's jelly, and cultured so as to give rise to chondrocytes that can produce cartilage tissue. The invention is based, in part, on the discovery that pre-chondrocytes can be isolated from Wharton's jelly by in vitro culturing techniques.

In one embodiment of the invention, a population of pre-chondrocytes isolated from Wharton's jelly is mitotically expanded and cultured in vitro to give rise to chondrocytes which can produce cartilage tissue for therapeutic use.

In another embodiment of the invention, pre-chondrocytes isolated from Wharton's jelly and/or chondrocytes differentiated therefrom, i.e., the cells of the invention, are cryopreserved and stored frozen in a "bank" from which they can be thawed and used to produce cartilage tissue as needed. For example, Wharton's jelly can be collected from a subject's umbilical cord shortly after the subject's birth. The cells of the invention, which are harvested or produced therefrom, can be stored frozen in a "bank" for a period of years, extending over the duration of the subject's life. The cells may be withdrawn from the bank as needed by thawing, and the thawed cells can be used to produce new tissues at any time during the subject's life for the repair, replacement or augmentation of cartilage, as well as other mesenchymal tissues, such as bone, tendon or ligament.

As a result of the "fetal" nature of the cells isolated from Wharton's jelly, immune rejection of the implanted cells of the invention, or cartilage tissue produced therefrom, may be minimized. Accordingly, in another embodiment of the invention, such cells are useful as "ubiquitous donor cells" for use in any subject in need thereof.

In another embodiment of the invention, the cells are suspended in a hydrogel solution where they can be either injected or implanted into a patient. Alternatively, the cells may be first seeded into the hydrogel, and then cultured prior to implantation. Preferably, the cells are cultured in the hydrogel so that they mitotically expand prior to implantation.

In yet another embodiment of the invention, new cartilage tissue is prepared from the cells of the invention and is used to repair, replace or augment cartilage tissue in a subject using any technique of repair, replacement or augmentation known in the art or to be developed in the future. For example, the cells of the invention may be seeded onto a three-dimensional framework or scaffold composed of a biocompatible non-living material having interstitial spaces, openings or pores that can be bridged by the pre-chondrocytes or chondrocytes. Under appropriate in vitro culture conditions, the seeded cells substantially envelope the three-dimensional framework and secrete an extracellular matrix to form a new, living cartilage tissue which can be implanted in vivo. Alternatively, the cells of the invention are seeded onto a three-dimensional framework and immediately implanted at a site in the subject. The seeded cells proceed to form new cartilage tissue in vivo.

In yet another embodiment, the three-dimensional framework on which the cells of the invention are seeded further comprises, or is coated with, one or more bioactive agents or other compounds selected from the group consisting of anti-inflammatories, growth factors, immunosuppressants, etc.

In yet another embodiment of the invention, the cells of the invention are inoculated and grown on a three-dimensional framework and placed in a container that can be manipulated to allow intermittent pressure changes, or in a bioreactor system specially designed for the in vitro production of cartilage tissue constructs, which bioreactor allows for pressurization of the chamber during growth and an adequate supply of nutrients to chondrocytes by convection.

In a further embodiment, the cells of the invention are administered directly to a site in vivo, e.g., by injection and without attachment to a three-dimensional framework, to produce new cartilage tissue at that site.

In a further embodiment of the invention, extracellular matrix is extracted from new cartilage tissue produced by the cells of the invention, and is further processed to a formulation that is useful for the repair or replacement of cartilage or for augmentation of facial or other body features, such as for cosmetic purposes.

In a further embodiment of the invention, the cells of the invention are stimulated to produce cartilage using exogenously supplied growth factors such as, for example, TGF-β or BMPs such as BMP-2, BMP-12 and BMP-13.

In yet another embodiment of the invention, the cells of the invention are genetically engineered to produce, or to increase production of, specific types of growth factors, peptides, proteins or other molecules that serve to increase the amount of cartilage produced, or that improve the success of implantation, for example, by reducing the risk of rejection or inflammation associated with the implant.

4. BRIEF DESCRIPTION OF THE DRAWINGS

FIG. 1A. New cartilage tissue formed in vitro on a cell-seeded three-dimensional framework. Cells of the invention were seeded onto a PGA felt framework, and cultured for 4 wk in complete medium (RPMI 1640, 10% FBS, 5% ES, antibiotic, antimycotic, without hydrocortisone), without TGF-β1. Magnification 4×. The ruler shown in the field is graded in millimeters.

Figure 1B:
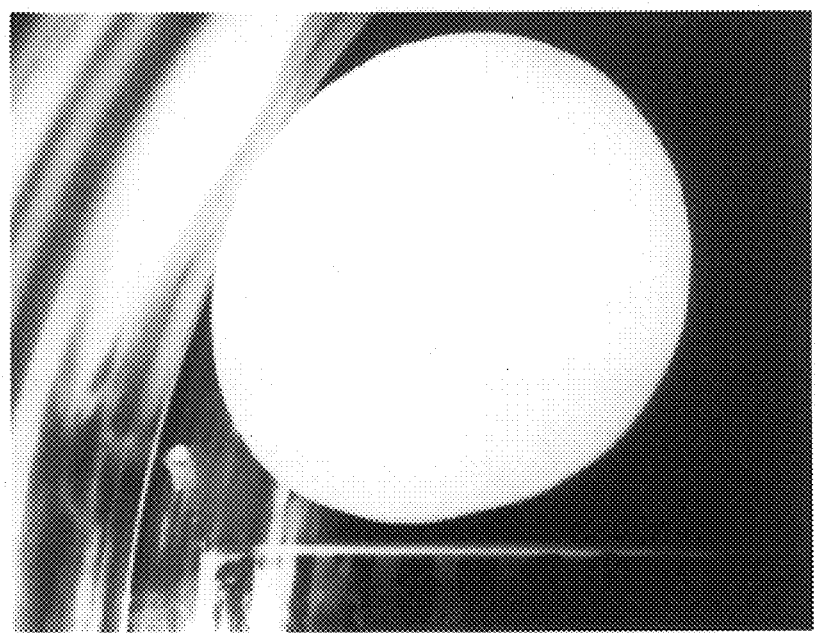

FIG. 1B. New cartilage tissue formed in vitro on a cell-seeded three-dimensional framework. Cells of the invention were seeded onto a PGA felt framework, followed by incubation for 72 hr in complete medium, (RPMI 1640, 10% FBS, 5% ES, antibiotic, antimycotic, without hydrocortisone), then in medium containing TGF-β1 (10 ng/mL) for 72 hr, and finally for an additional three weeks in complete medium without TGF-β1. Magnification 4×. The ruler shown in the field is graded in millimeters. The cartilage is larger and more dense than that of FIG. 1A.

Figure 1C:
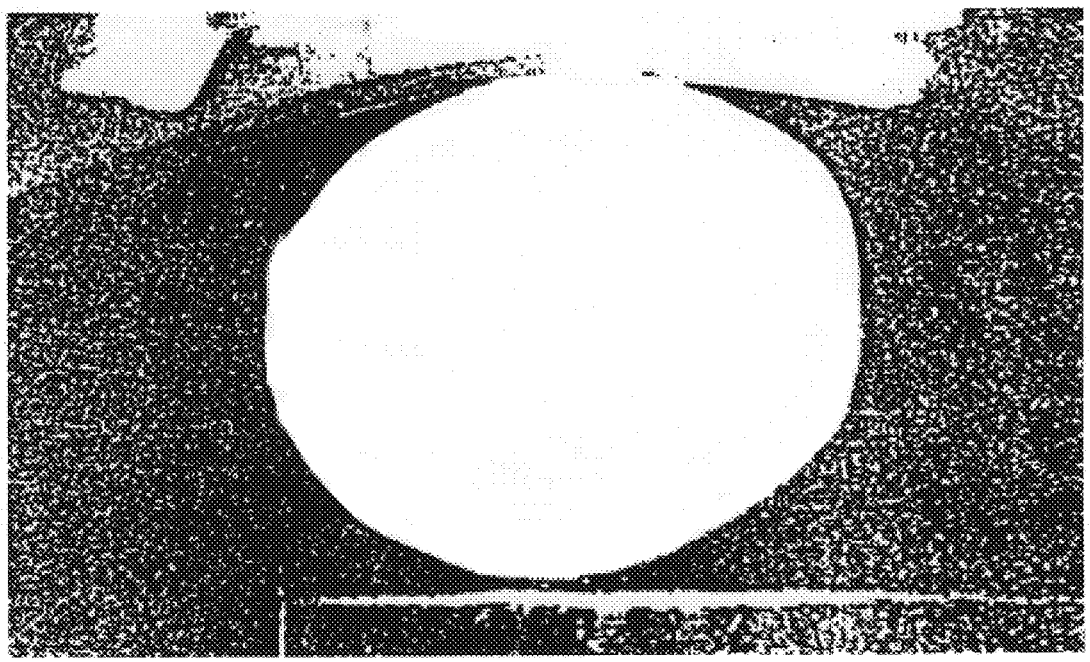

FIG. 1C. New cartilage tissue formed in vitro on a cell-seeded three-dimensional framework. Cells of the invention were seeded onto a PGA felt framework, followed by incubation for 72 hr in complete medium, (RPMI 1640, 10% FBS, 5% ES, antibiotic, antimycotic, without hydrocortisone), then in medium containing TGF-β1 (10 ng/mL) for 72 hr. The cell construct was then cultured in complete media without TGF-β1 for 72 hours. TGF-β1 (10 ng/mL) was then added for another 72 hour period. Finally, the cell construct was cultured for an additional 2.5 weeks in a complete medium without TGF-β1. Magnification 4×. The ruler shown in the field is graded in millimeters. The cartilage is larger and more dense than that of FIG. 1A.

Figure 2A:
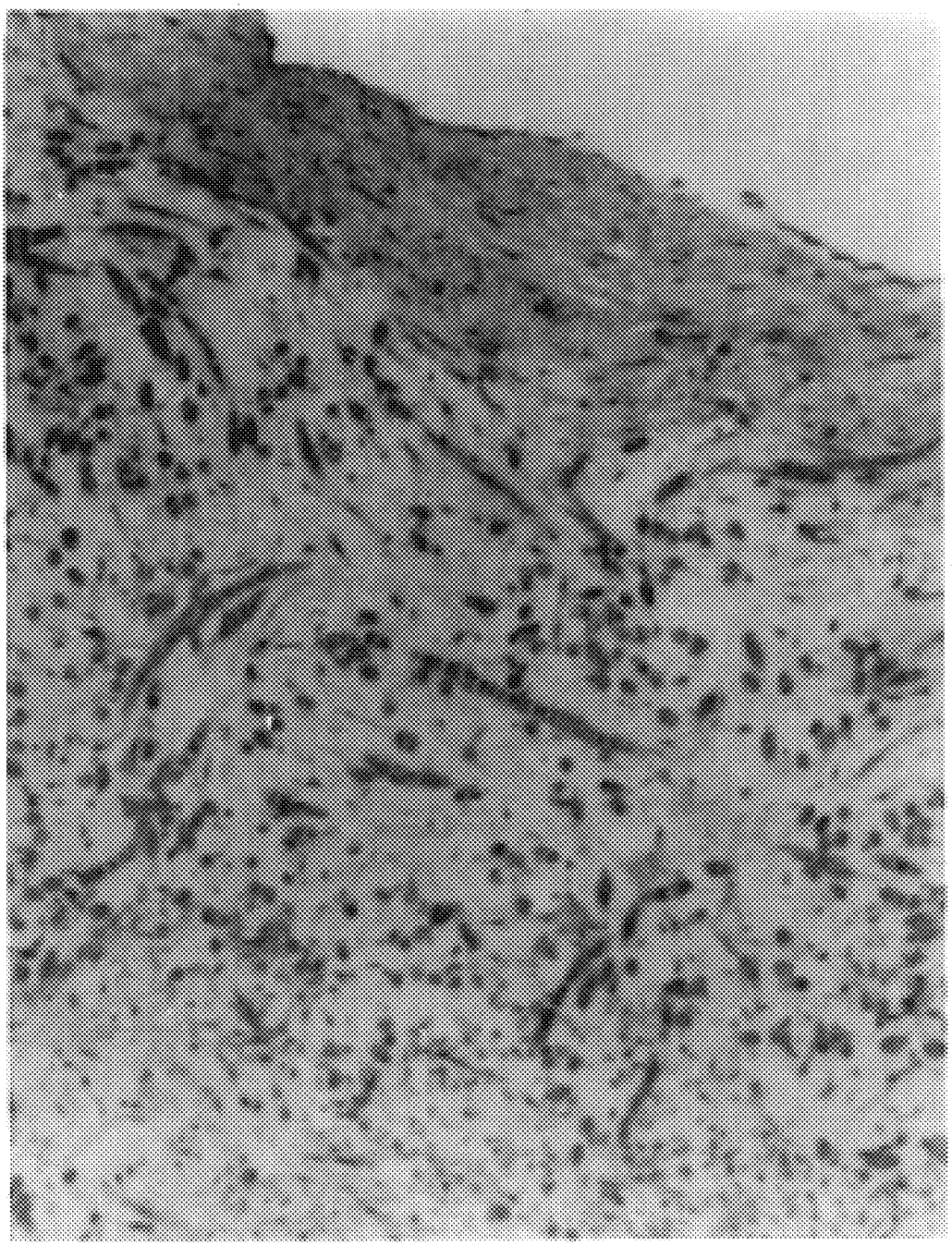

FIG. 2A. Hematoxylin and eosin stained sections (4 μm) of new cartilage tissue which was cultured as described in FIG. 1B. The tissue shows extensive matrix deposition but the lacunae which are characteristic of hyaline cartilage are absent. Magnification 100×.

Figure 2B:
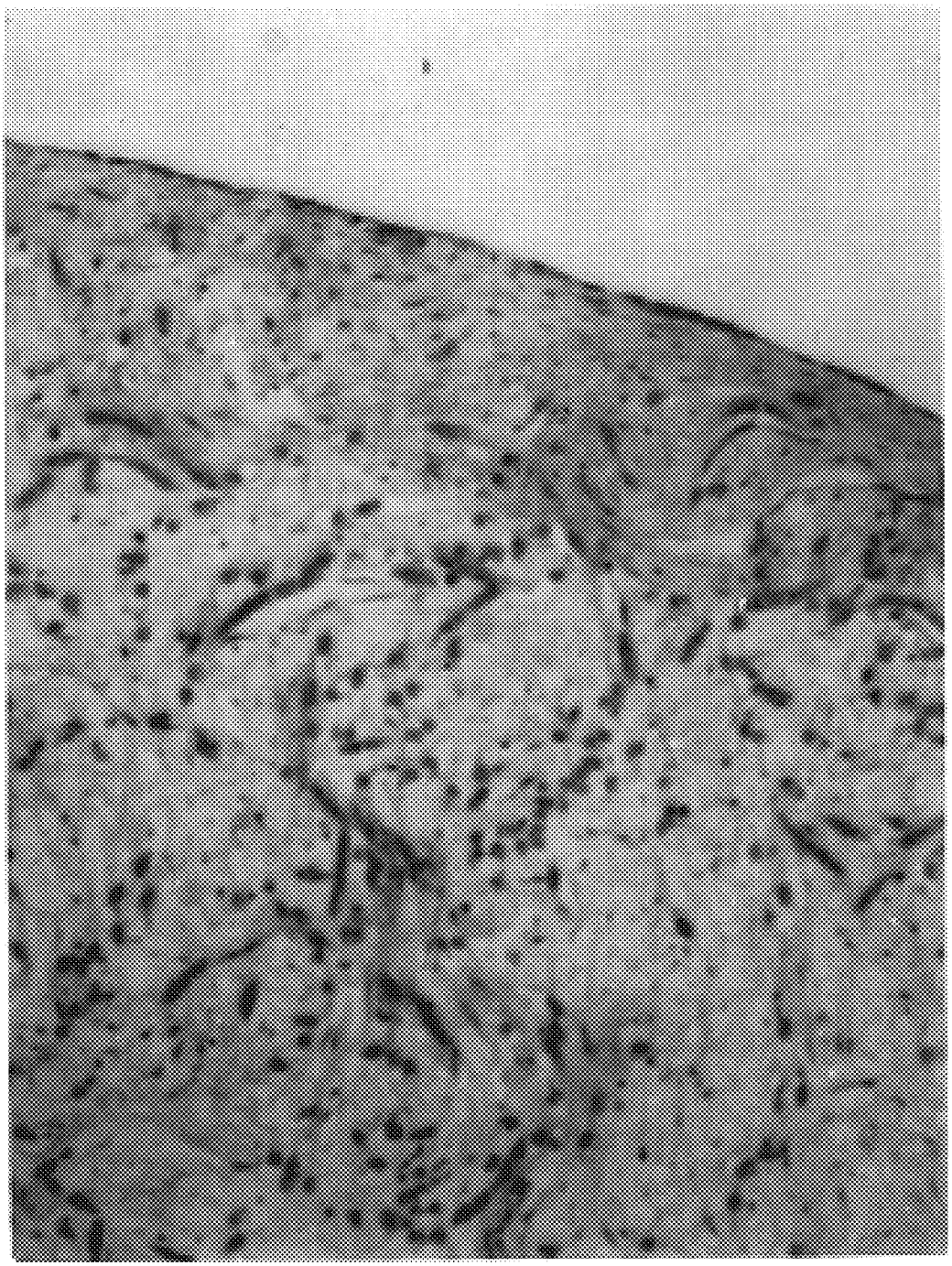

FIG. 2B. Hematoxylin and eosin stained sections (4 μm) of new cartilage tissue which was cultured as described in FIG. 1C. The tissue shows extensive matrix deposition but the lacunae which are characteristic of hyaline cartilage are absent. Magnification 100×.

Figure 3A:
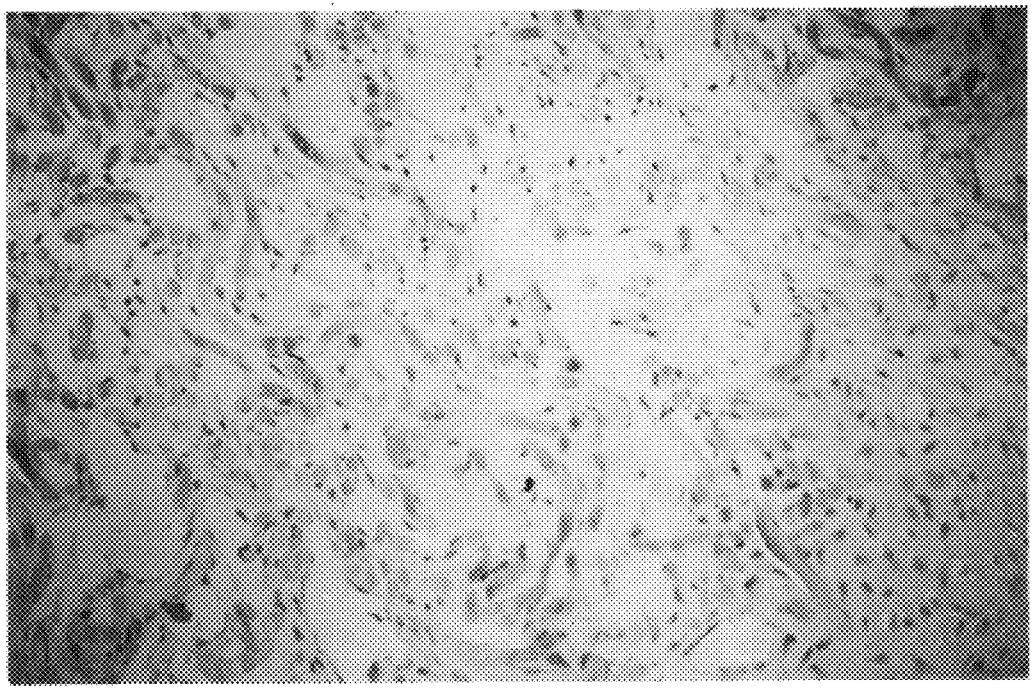

FIG. 3A. Safronin O stained sections (7–8 μm) of new cartilage tissue which was cultured as described in FIG. 1B. Magnification 100×.

Figure 3B:
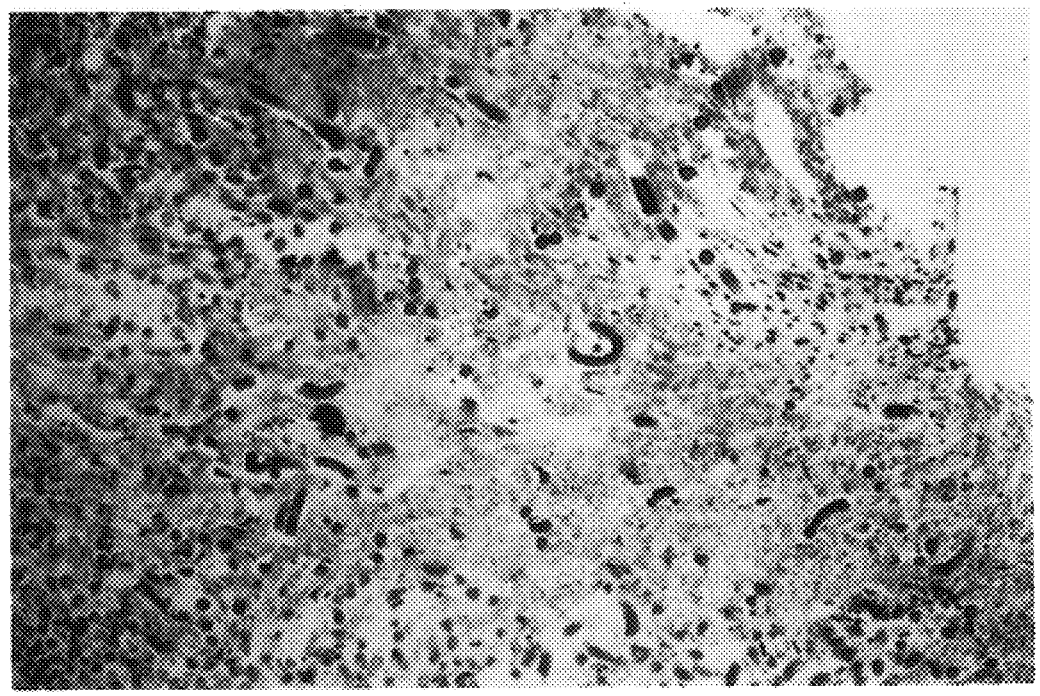

FIG. 3B. Trichrome stained sections (7–8 μm) of new cartilage tissue which was cultured as described in FIG. 1B. Magnification 100×.

Figure 4A:
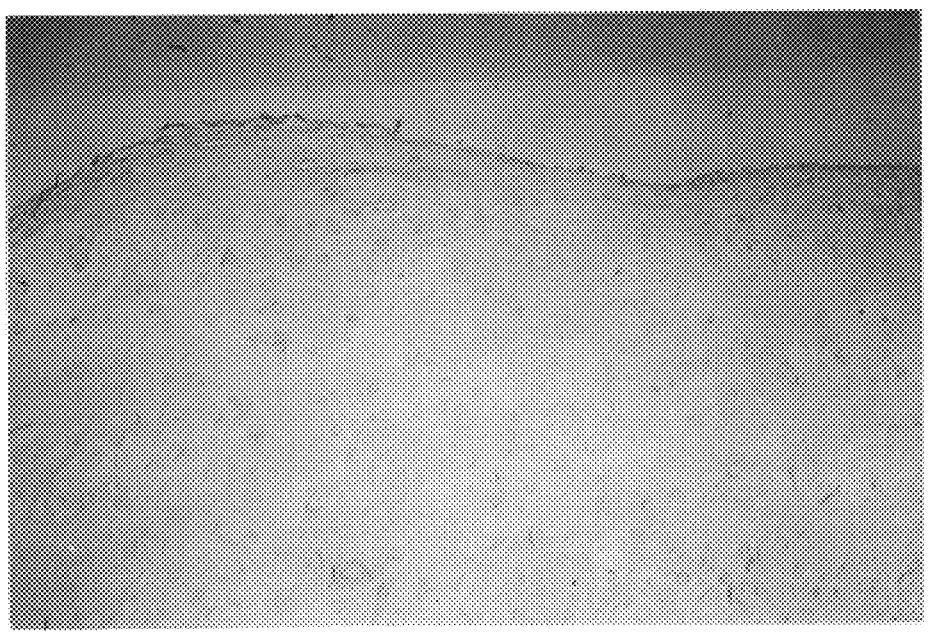

FIG. 4A. Immunostaining: section (4 μm) of new cartilage tissue which was cultured as described in FIG. 1B. Section was treated with normal serum (isotypic control). Staining was developed using the immunoperoxidase reaction. Magnification 100×

Figure 4B:
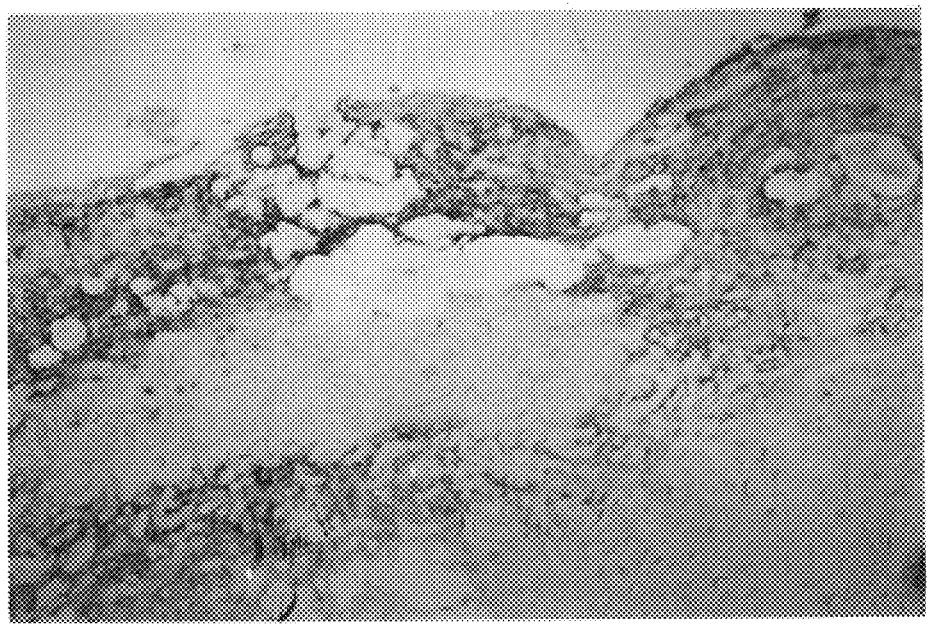

FIG. 4B. Immunostaining: section (4 μm) of new cartilage tissue which was cultured as described in FIG. 1B. Section was treated with antibodies to human type I. Staining was developed using the immunoperoxidase reaction which resulted in positive staining for type I collagen. Magnification 100×

Figure 4C:
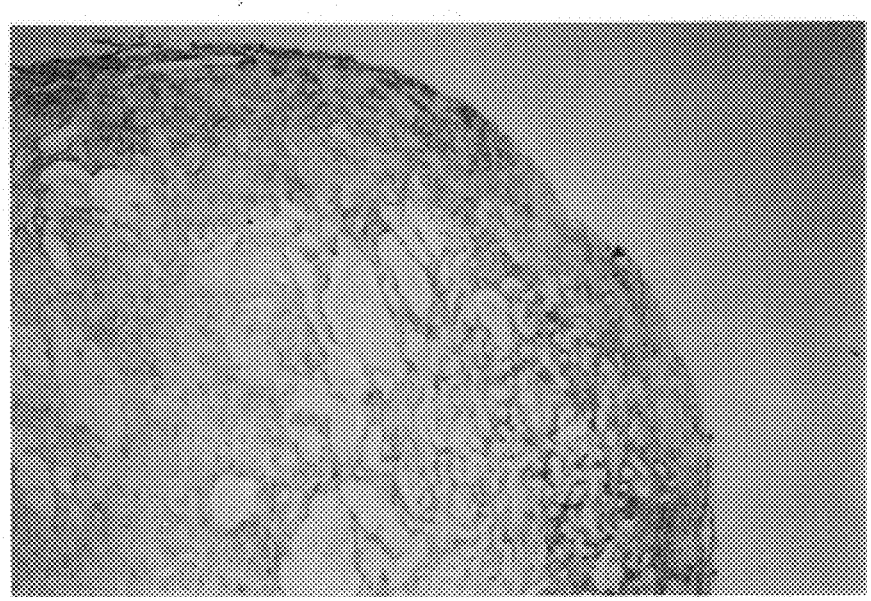

FIG. 4C. Immunostaining: section (4 μm) of new cartilage tissue which was cultured as described in FIG. 1B. Section was treated with antibodies to human type II. Staining was developed using the immunoperoxidase reaction which resulted in positive staining for type II collagen. Magnification 100×

Figure 4D:
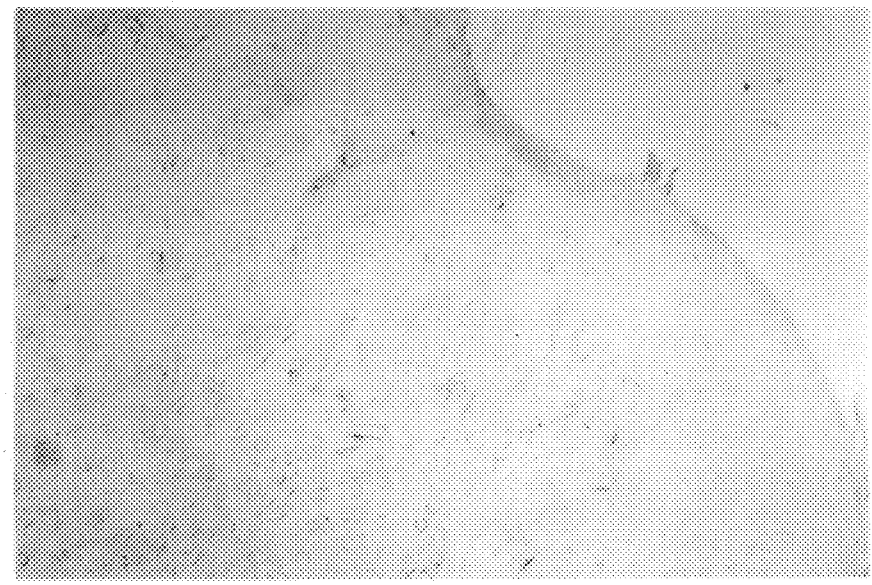

FIG. 4D. Immunostaining: section (4 μm) of new cartilage tissue which was cultured as described in FIG. 1C. Section was treated with antibodies to human type I collagen. Staining was developed using the immunoperoxidase reaction which resulted in positive staining for type I collagen. Magnification 100×

Figure 4E:
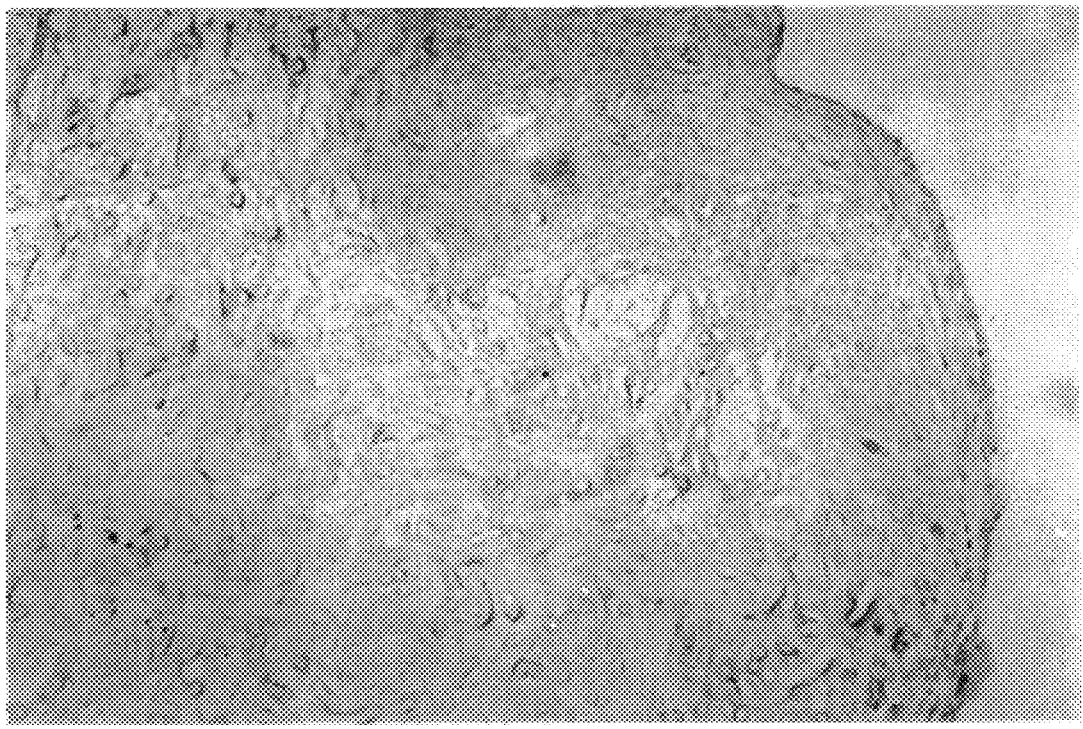

FIG. 4E. Immunostaining: section (4 μm) of new cartilage tissue which was cultured as described in FIG. 1C. Section was treated with antibodies to human type II collagen. Staining was developed using the immunoperoxidase reaction which resulted in positive staining for type II collagen. Magnification 100×

Figure 5:
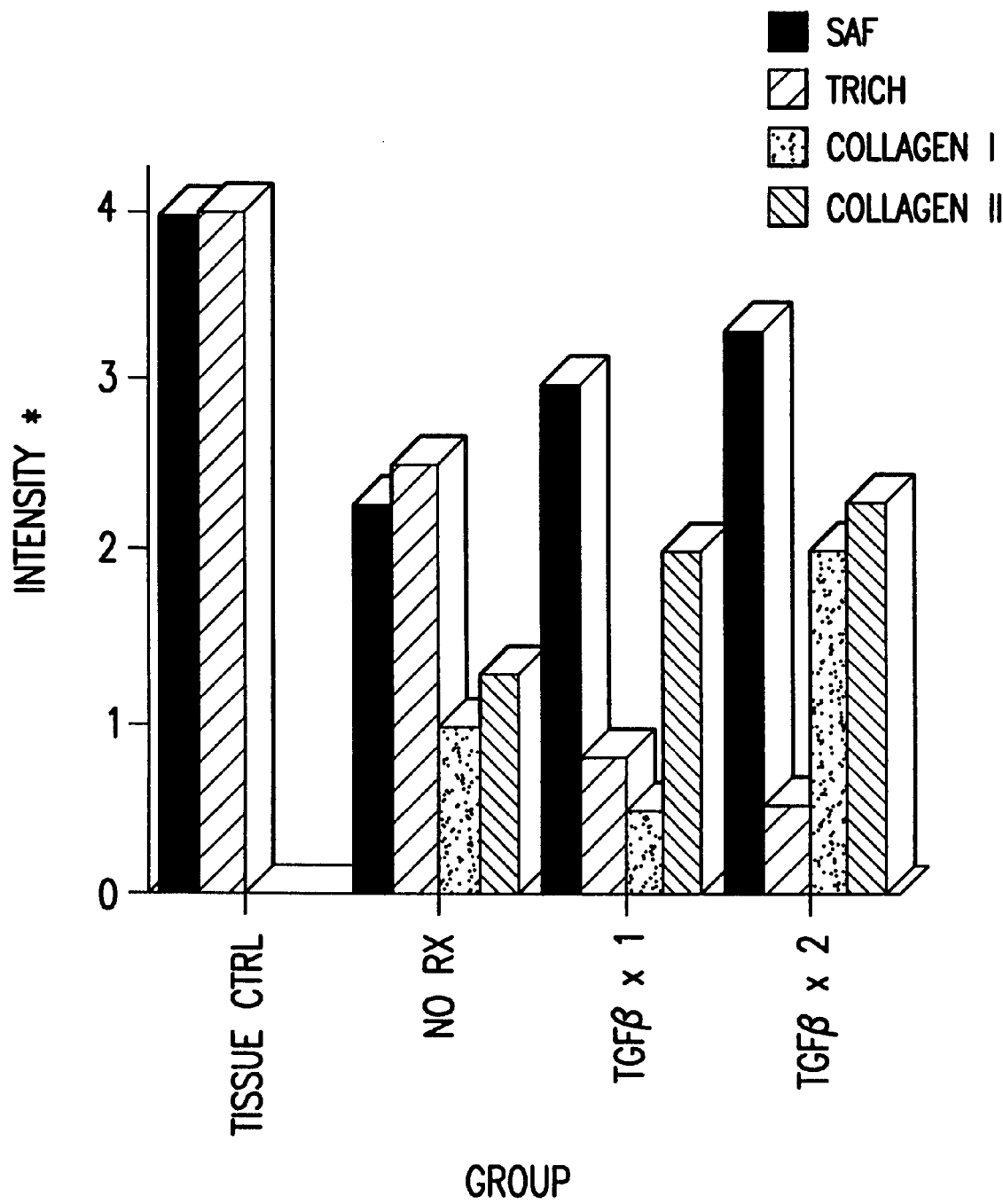

FIG. 5. Summary of the staining intensities of the new cartilage tissue constructs. Cultures were performed as described as above in FIGS. 1A (no TGF-β1, e.g., no treatment), 1B (TGF-β1×1), and 1C (TGF-β1×2). Intensities were graded on a 0 to +4 scale. Staining of constructs with safronin O (SAF) and trichrome (TRICH) staining was compared to staining of articular cartilage tissue sections (positive control, +4). Immunostaining of constructs with antibodies to type I or type II collagen followed by immunoperoxidase reaction was compared to staining with isotypic control serum (negative control, O).

Figure 6A:
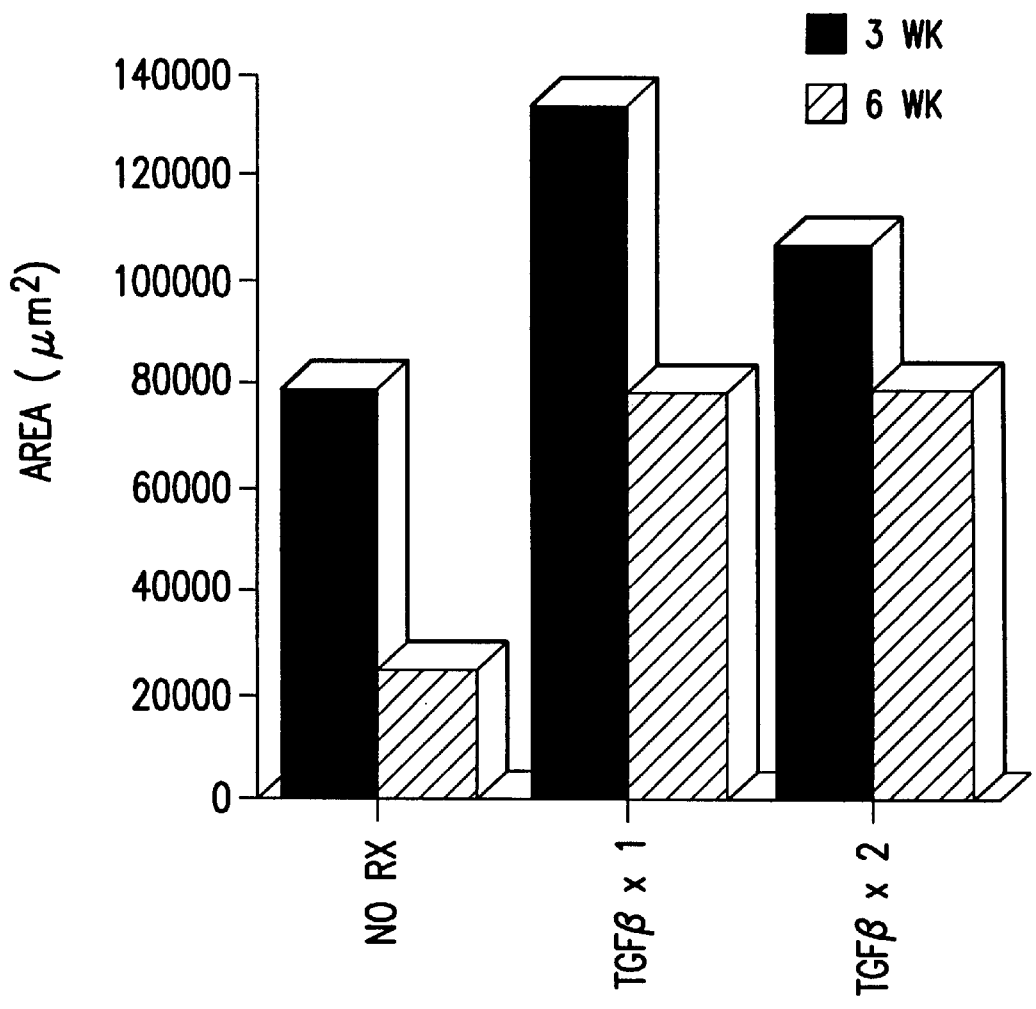

FIG. 6A. Area (μm$^2$) of longitudinal sections of the new cartilage tissue constructs. The 3 week cultures were performed as described above in FIGS. 1A (no TGF-β1), 1B (TGF-β1×1), and 1C (TGF-β1×2) cultured for a total of 3 weeks. The 6 week cultures were carried out as above but were continued in culture for an additional 3 weeks in a complete medium without TGF-β1. Areas were measured by computer assisted planimetry. This data quantifies what was shown in FIGS. 1A–C. The greatest incremental increase was observed over an about 3 week period.

Figure 6B:
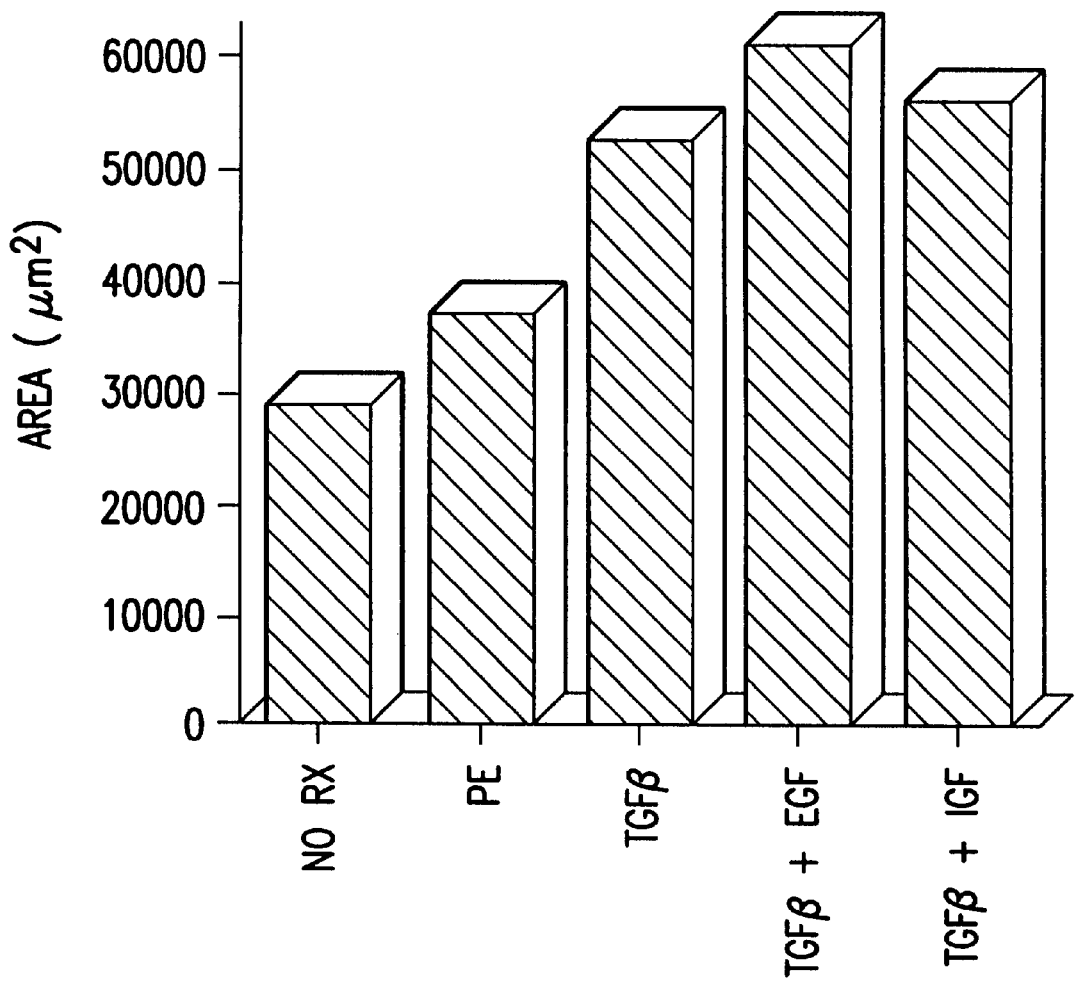

FIG. 6B. Area (μm$^2$) of longitudinal sections of the new cartilage tissue constructs after 3 weeks in culture. Cultures were either not treated or treated with the following growth factors: pituitary extract (PE, 10 μg/mL) where the cells of the invention were seeded onto a PGA felt framework, followed by incubation for 72 hr in complete medium, (RPMI 1640, 10% FBS, 5% ES, antibiotic, antimycotic, without hydrocortisone), then in medium containing PE (10 μg/mL) for 72 hr, and finally for an additional three weeks in complete medium without PE; TGF-β1 plus epidermal growth factor (EGF, 100 ng/mL) added in the manner described in FIG. 1B except that epidermal growth factor was added along with the TGF-β1; TGF-β1 plus insulin-like growth factor (IGF, 100 ng/mL) added in the manner described in FIG. 1B except that insulin-like growth factor was added along with the TGF-β1. Areas were measured by computer assisted planimetry. These data show that other factors influence the growth of collagen tissue.

5. DETAILED DESCRIPTION OF THE INVENTION

The present invention relates to compositions and methods for the production of new cartilage tissue for use in treating disease or injury of cartilage, or augmenting structures by providing additional cartilage, involving: (a) methods for isolating pre-chondrocytes from Wharton's jelly of umbilical cord; (b) methods for mitotically expanding the populations of isolated pre-chondrocytes and/or chondrocytes differentiated therefrom, hereinafter collectively known as the cells of the invention; and (c) methods for culturing mitotically expanded populations of the cells of the invention under conditions that permit or induce the formation of new cartilage tissue. The invention also relates to the products of the foregoing methods, including but not limited to, the cells of the invention, mitotically expanded or otherwise; new cartilage tissue produced therefrom; extracellular matrix extracted therefrom; and three-dimensional cartilage/framework constructs. The invention also relates to the use of these cells, constructs and tissues in vivo to repair, replace or augment cartilage, or in vitro to form three-dimensional cartilage cultures which are useful to produce new cartilage tissue or bioactive agents, or to test the cytotoxicity of potential therapeutic agents or cosmetics.

The pre-chondrocytes isolated from Wharton's jelly, as well as the chondrocytes differentiated therefrom, can be used to produce new cartilage tissue to repair or replace cartilage lost to disease or trauma. In addition, the cells of the invention can be cryopreserved and stored frozen, thus establishing "banks" of cells that can be used to produce new cartilage tissue at any time during a subject's life to replace cartilage lost to disease or trauma. The invention is further intended to include the use of the cells of the invention, in a bank or otherwise, as "ubiquitous donor cells" to produce cartilage tissue for use in any subject in need thereof.

The term "pre-chondrocyte" as used herein refers either to: (1) a pluripotent, or lineage-uncommitted, progenitor cell, typically referred to in the art as a "stem cell", which is potentially capable of an unlimited number of mitotic divisions to either renew its line or to produce progeny cells which will differentiate into chondrocytes; or (2) a lineage-committed progeny cell produced from the mitotic division of a stem cell which will eventually differentiate into a chondrocyte. Unlike the stem cell from which it is derived, the lineage-committed progeny cell is generally considered to be incapable of an unlimited number of mitotic divisions to produce other progeny cells, but instead will eventually differentiate into a chondrocyte.

The term "chondrocyte" as used herein refers to: (1) a cell that has differentiated from a pre-chondrocyte; or (2) a cell that has arisen from the mitotic division of a parent chondrocyte; or (3) any cell derived from umbilical cord sources, such as Wharton's jelly, that is capable of secreting an extracellular matrix ("ECM") that, by itself or in combination with one or more other cells, produces and/or comprises cartilage tissue.

The term "cells of the invention" as used herein refers to (1) pre-chondrocytes isolated from umbilical cord sources, such as Wharton's jelly; (2) chondrocytes; or (3) mixed populations of the aforementioned pre-chondrocytes and chondrocytes.

The term "cartilage tissue" is used herein as that term is generally recognized in the art, and refers to a specialized type of dense connective tissue comprising cells embedded in an ECM (see, for example, Cormack, 1987, *Ham's Histology*, 9th Ed., J.B. Lippincott Co., pp. 266–272). The biochemical composition of cartilage differs according to type; however, the general composition of cartilage comprises chondrocytes surrounded by a dense ECM consisting of collagen, proteoglycans and water. Several types of cartilage are recognized in the art, including, for example, hyaline cartilage, articular cartilage, costal cartilage, fibrous cartilage, meniscal cartilage, elastic cartilage, auricular cartilage, and yellow cartilage. The production of any type of cartilage is intended to fall within the scope of the invention.

The invention is directed predominantly to compositions and methods for the production of new cartilage tissue for use in humans. However, the invention may also be practiced so as to produce new cartilage tissue for use in any mammal in need thereof, including horses, dogs, cats, sheep, pigs, among others. The treatment of such animals is intended to fall within the scope of the invention.

The invention is divided into the following sections solely for the purpose of description: (i) isolation of pre-chondrocytes from Wharton's jelly; (ii) differentiation of chondrocytes and the production of new cartilage tissue; (iii) establishment of "banks" of pre-chondrocytes and/or chondrocytes; (iv) uses of pre-chondrocytes and chondrocytes in vivo; (v) establishment of three-dimensional cartilage cultures in vitro; (vi) uses for new cartilage tissue; and (vii) genetically engineered cartilage.

5.1. Isolation of Pre-Chondrocytes from Wharton's Jelly

The pre-chondrocytes of the invention are isolated from umbilical cord sources, preferably from Wharton's jelly. Wharton's jelly is a gelatinous substance found in the umbilical cord which has been generally regarded as a loose mucous connective tissue, and has been frequently described as consisting of fibroblasts, collagen fibers and an amorphous ground substance composed mainly of hyaluronic acid (Takechi et al., 1993, Placenta 14:235–45). Various studies have been carried out on the composition and organization of Wharton's jelly (Gill and Jarjoura, 1993, J. Rep. Med. 38:611–614; Meyer et al., 1983, Biochim. Biophys. Acta 755:376–387). One report described the isolation and in vitro culture of "fibroblast-like" cells from Wharton's jelly (McElreavey et al., 1991, Biochem. Soc. Trans. 636th Meeting Dublin 19:29S).

To collect Wharton's jelly for the isolation and culture of pre-chondrocytes according to the invention, umbilical cord is obtained immediately upon termination of either a full term or pre-term pregnancy. For example, but not by way of limitation, the umbilical cord, or a section thereof, may be transported from the birth site to the laboratory in a sterile container such as a flask, beaker or culture dish, containing a medium, such as, for example, Dulbecco's Modified Eagle's Medium (DMEM). The umbilical cord is preferably maintained and handled under sterile conditions prior to and during collection of the Wharton's jelly, and may additionally be surface-sterilized by brief surface treatment of the cord with, for example, a 70% ethanol solution, followed by a rinse with sterile, distilled water. The umbilical cord can be briefly stored for up to about three hours at about 3–5° C., but not frozen, prior to extraction of the Wharton's jelly.

Wharton's jelly is collected from the umbilical cord under sterile conditions by any appropriate method known in the art. For example, the cord is cut transversely with a scalpel, for example, into approximately one inch sections, and each section transferred to a sterile container, such as a 50 ml centrifuge tube, containing a sufficient volume of phosphate buffered saline (PBS) containing $CaCl_2$ (0.1 g/l) and $MgCl_2 \cdot 6 H_2O$ (0.1 g/l) to allow surface blood to be removed from the section upon gentle agitation. The section is then removed to a sterile-surface where the outer layer or "casing" of the section is sliced open along the cord's longitudinal axis. Wharton's jelly is typically located between the three blood vessels of the umbilical cord. The blood vessels and casing are dissected away, for example, with sterile forceps and dissection scissors, and the Wharton's jelly is collected and placed in a sterile container, such as a 100 mm TC-treated Petri dish. The Wharton's jelly may then be cut into smaller sections, such as 2–3 $mm^3$, for culturing.

Wharton's jelly is incubated in vitro in culture medium under appropriate conditions to permit the proliferation of any pre-chondrocytes present therein. Any appropriate type of culture medium can be used to isolate the pre-chondrocytes of the invention, such as, but not limited to, DMEM, McCoys 5A medium (Gibco), Eagle's basal medium, CMRL medium, Glasgow minimum essential medium, Ham's F-12 medium, Iscove's modified Dulbecco's medium, Liebovitz' L-15 medium, and RPMI 1640, among others. The culture medium may be supplemented with one or more components including, for example, fetal bovine serum (FBS), equine serum (ES), HUMAN SERUM (HS), and one or more antibiotics and/or antimycotics to control microbial contamination, such as, for example, penicillin G, streptomycin sulfate, amphotericin B, gentamicin, and nystatin, either alone or in combination, among others.

Methods for the selection of the most appropriate culture medium, medium preparation, and cell culture techniques are well known in the art and are described in a variety of sources, including Doyle et al., (eds.), 1995, *Cell & Tissue Culture: Laboratory Procedures*, John Wiley & Sons, Chichester; and Ho and Wang (eds.), 1991, *Animal Cell Bioreactors*, Butterworth-Heinemann, Boston, which are incorporated herein by reference.

After culturing Wharton's jelly for a sufficient period of time, for example, about 10–12 days, pre-chondrocytes present in the explanted tissue will tend to have grown out from the tissue, either as a result of migration therefrom or cell division, or both. These pre-chondrocytes may then be removed to a separate culture vessel containing fresh medium of the same or a different type as that used initially, where the population of pre-chondrocytes can be mitotically expanded.

Alternatively, the different cell types present in Wharton's jelly can be fractionated into subpopulations from which pre-chondrocytes can be isolated. This may be accomplished using standard techniques for cell separation including, but not limited to, enzymatic treatment to dissociate Wharton's jelly into its component cells, followed by cloning and selection of specific cell types, using either morphological or biochemical markers, selective destruction of unwanted cells (negative selection), separation based upon differential cell agglutinability in the mixed population as, for example, with soybean agglutinin, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis, and fluorescence activated cell sorting (FACS). For a review of clonal selection and cell separation techniques, see Freshney, 1994, *Culture of Animal Cells; A Manual of Basic Techniques*, 3d Ed., Wiley-Liss, Inc., New York, which is incorporated herein by reference.

In a preferred embodiment for culturing pre-chondrocytes, Wharton's jelly is cut into sections of approximately 2–3 $mm^3$, and placed in a TC-treated Petri dish containing glass slides on the bottom of the Petri dish. The tissue sections are then covered with another glass slide and cultured in a complete medium, such as, for example, RPMI 1640 containing 10% FBS, 5% ES and antimicrobial compounds, including penicillin G (100 $\mu$g/ml), streptomycin sulfate (100 $\mu$g/ml), amphotericin (250 $\mu$g/ml), and gentamicin (10 $\mu$g/ml), pH 7.4–7.6. The tissue is preferably incubated at 37° C. and 5% $CO_2$ for 10–12 days.

The medium is changed as necessary by carefully aspirating the medium from the dish, for example, with a pipette, and replenishing with fresh medium. Incubation is continued as above until a sufficient number or density of cells accumulate in the dish and on the surfaces of the slides. For example, approximately 70 percent confluence but not to the point of complete confluence. The original explanted tissue sections may be removed and the remaining cells are trypsinized using standard techniques. After trypsinization, the cells are collected, removed to fresh medium and incubated as above. The medium is changed at least once at 24 hr post-trypsin to remove any floating cells. The cells remaining in culture are considered to be pre-chondrocytes.

Once the pre-chondrocytes have been isolated, their population is expanded mitotically. The pre-chondrocytes should be transferred or "passaged" to fresh medium when they reach an appropriate density, such as 3 to $6.5 \times 10^4/cm^2$, or, for example, when they reach a defined percentage of confluency on the surface of a culture dish. During incubation of the pre-chondrocytes, cells can stick to the walls of the culture vessel where they can continue to proliferate and form a confluent monolayer. This should be prevented or minimized, for example, by transferring a portion of the cells to a new culture vessel having fresh medium, since the presence of a confluent monolayer in the culture vessel will tend to "shut down" the growth of cells in the culture. Removal of the confluent monolayer or transfer of a portion of the cells to fresh media in a new vessel will usually restore proliferative activity of the cells. Such removal or transfer should be done in any culture vessel which has a pre-chondrocyte monolayer exceeding about 25% confluency. Alternatively, the liquid culture can be agitated, for example, on an orbital shaker, to prevent the cells from sticking to the vessel walls.

In a preferred embodiment, cartilage tissue is produced using pre-chondrocytes that have gone through a low number of passages. For example, 2–4 passages appear to be an optimal number of passages to preserve the ability of the cells to differentiate and produce cartilage tissue. However, the invention contemplates that once pre-chondrocytes have been established in culture, their ability to serve as progenitors for chondrocytes that can produce cartilage can be maintained, for example, by regular passage to fresh medium as the cell culture reaches an appropriate density or percentage of confluency, or by treatment with an appropriate growth factor, or by modification of the culture medium or culture protocol, or by some combination of the above.

According to the invention, pre-chondrocytes may be obtained from Wharton's jelly collected from a subject's own umbilical cord. Alternatively, it may be advantageous to obtain pre-chondrocytes from Wharton's jelly obtained from an umbilical cord associated with a developing fetus or newly-born child, where the subject in need of treatment is one of the parents of the fetus or child. Alternatively, because of the "fetal" nature of cells isolated from Wharton's jelly, immune rejection of the cells of the invention and/or the new cartilage tissue produced therefrom may be minimized. As a result, such cells may be useful as "ubiquitous donor cells" for the production of new cartilage tissue for use in any subject in need thereof.

5.2. Differentiation of Chondrocytes and the Production of Cartilage Tissue

Once established, a culture of pre-chondrocytes may be used to produce chondrocytes capable of producing new cartilage tissue. Differentiation of pre-chondrocytes to chondrocytes, followed by the production of cartilage tissue therefrom, can be triggered by the addition to the culture medium of specific exogenous growth factors, such as, for example, BMPs such as BMP-13 or TGF-$\beta$, with or without ascorbate.

Alternatively, pre-chondrocytes can be genetically engineered to express genes for specific types of growth factors such as, for example, TGF-$\beta$ (e.g., TGF-$\beta_1$), for successful and/or improved differentiation to chondrocytes and/or turnover of cartilage production either pre- or post-implantation. As well as TIMPs or tissue inhibitors of metallo proteinases.

The invention further contemplates the establishment and maintenance of cultures of chondrocytes as well as mixed cultures comprising both pre-chondrocytes and chondrocytes. As with pre-chondrocytes, once a culture of chondrocytes or a mixed culture of pre-chondrocytes and chondrocytes is established, the population of cells is mitotically expanded in vitro by passage to fresh medium as cell density dictates, under conditions conducive to cell proliferation without cartilage formation, such as, for example, in culture medium lacking TGF-$\beta$ or other growth factor. As with cultures of pre-chondrocytes, cultures of chondrocytes and mixed cultures of pre-chondrocytes and chondrocytes should be transferred to fresh medium when sufficient cell density is reached. Thus, formation of a monolayer of cells should be prevented or minimized, for example, by transferring a portion of the cells to a new culture vessel and into fresh medium. Such removal or transfer should be done in any culture vessel which has a cellular monolayer exceeding about 25% confluency. Alternatively, the culture system can be agitated to prevent the cells from sticking.

5.3. Establishment of Cell Banks

Once the cells of the invention have been established in culture, as described above, they may be maintained or stored in cell "banks" comprising either continuous in vitro cultures of cells requiring regular transfer, or, preferably, cells which have been cryopreserved.

Cryopreservation of cells of the invention may be carried out according to known methods, such as those described in Doyle et al., 1995, supra. For example, but not by way of limitation, cells may be suspended in a "freeze medium" such as, for example, culture medium further comprising 15–20% FBS and 10% dimethylsulfoxide (DMSO), with or without 5–10% glycerol, at a density, for example, of about 4–10$\times 10^6$ cells/ml. The cells are dispensed into glass or plastic ampoules (Nunc) which are then sealed and transferred to the freezing chamber of a programmable freezer. The optimal rate of freezing may be determined empirically. For example, a freezing program that gives a change in temperature of –1° C./min through the heat of fusion may be used. Once the ampoules have reached –180° C., they are transferred to a liquid nitrogen storage area. Cryopreserved cells can be stored for a period of years, though they should be checked at least every 5 years for maintenance of viability.

The cryopreserved cells of the invention constitute a bank of cells, portions of which can be "withdrawn" by thawing and then used to produce new cartilage tissue as needed. Thawing should generally be carried out rapidly, for example, by transferring an ampoule from liquid nitrogen to a 37° C. water bath. The thawed contents of the ampoule should be immediately transferred under sterile conditions to a culture vessel containing an appropriate medium such as RPMI 1640 conditioned with 10% FBS and 5% ES. It is advisable that the cells in the culture medium be adjusted to an initial density of about 3–6$\times 10^5$ cells/ml so that the cells can condition the medium as soon as possible, thereby preventing a protracted lag phase. Once in culture, the cells may be examined daily, for example, with an inverted microscope to detect cell proliferation, and subcultured as soon as they reach an appropriate density.

The cells of the invention may be withdrawn from the bank as needed, and used for the production of new cartilage tissue either in vitro, for example, as a three dimensional cartilage culture, as described below, or in vivo, for example, by direct administration of cells to the site where new cartilage tissue is needed. As described supra, the cells of the invention may be used to produce new cartilage tissue for use in a subject where the cells were originally isolated from that subject's umbilical cord (autologous). Alternatively, the cells of the invention may be used as ubiquitous donor cells, i.e., to produce new cartilage tissue for use in any subject (heterologous).

5.4. Uses of Pre-Chondrocytes and Chondrocytes in Vivo

The cells of the invention may be used to treat subjects requiring the repair or replacement of cartilage tissue resulting from disease or trauma, or to provide a cosmetic function, such as to augment facial or other features of the body. Treatment may entail the use of the cells of the invention to produce new cartilage tissue, and the use of the cartilage tissue thus produced, according to any method presently known in the art or to be developed in the future. For example, the cells of the invention may be implanted, injected or otherwise administered directly to the site of tissue damage so that they will produce new cartilage tissue in vivo.

In a non-limiting embodiment, a formulation comprising the cells of the invention is prepared for injection directly to the site where the production of new cartilage tissue is desired. For example, and not by way of limitation, the cells of the invention may be suspended in a hydrogel solution for injection. Alternatively, the hydrogel solution containing the cells may be allowed to harden, for instance in a mold, to form a matrix having cells dispersed therein prior to implantation. Or, once the matrix has hardened, the cell formations may be cultured so that the cells are mitotically expanded prior to implantation. The hydrogel is an organic polymer (natural or synthetic) which is cross-linked via convalent, ionic, or hydrogen bonds to create a three-dimensional open-lattice structure which entraps water molecules to form a gel. Examples of materials which can be used to form a hydrogel include polysaccharides such as alginate and salts thereof, polyphosphazines, and polyacrylates, which are cross-linked ionically, or block polymers such as Pluronics™ or Tetronics™, polyethylene oxide-polypropylene glycol block copolymers which are cross-linked by temperature or pH, respectively.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is cross-linked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure (1):

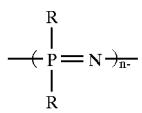

where n is an integer.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are cross-linked by divalent or trivalent cations such as $Ca^{2+}$ or $Al^{3+}$. Polymers can be synthesized that degrade by hydrolysis by incorporating monomers having imidazole, amino acid ester, or glycerol side groups.

For example, a polyanionic poly[bis(carboxylatophenoxy)] phosphazene (PCPP) can be synthesized, which is cross-linked with dissolved multivalent cations in aqueous media at room temperature or below to form hydrogel matrices.

Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegradable, as used herein, means a polymer that dissolves or degrades within a period that is acceptable in the desired application (usually in vivo therapy), less than about five years and most preferably less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824–830 (1977). Methods of synthesis of the hydrogel materials, as well as methods for preparing such hydrogels, are known in the art.

Such cell formulations may further comprise one or more other components, including selected extracellular matrix components, such as one or more types of collagen known in the art, and/or growth factors and drugs. Growth factors which may be usefully incorporated into the cell formulation include one or more tissue growth factors known in the art or to be identified in the future, such as but not limited to any member of the TGF-β family, IGF-I and -II, growth hormone, BMPs such as BMP-13, etc. Alternatively, the cells of the invention may be genetically engineered to express and produce for growth factors such as BMP-13 or TGF-β. Details on genetic engineering of the cells of the invention are provided infra. Drugs which may be usefully incorporated into the cell formulation include anti-inflammatory compounds, as well as local anesthetics. Other components may also be included in the formulation, including but not limited to any of the following: (1) buffers to provide appropriate pH and isotonicity; (2) lubricants; (3) viscous materials to retain the cells at or near the site of administration, including, for example, alginates, agars and plant gums; and (4) other cell types that may produce a desired effect at the site of administration, such as, for example, enhancement or modification of the formation of cartilage tissue or its physicochemical characteristics, or support for the viability of the cells, or inhibition of inflammation or rejection. The cells may be covered by an appropriate wound covering to prevent cells from leaving the site. Such wound coverings are known as those of skill in the art.

Alternatively, the cells of the invention may be seeded onto a three-dimensional framework or scaffold and immediately implanted in vivo, where the seeded cells will proliferate on the surface of the framework and form a replacement cartilage tissue in vivo in cooperation with the cells of the subject. Details on the use of a three-dimensional framework are provided infra. Such a framework can be implanted in combination with any one or more growth factors, drugs or other components described above that stimulate cartilage formation or otherwise enhance or improve the practice of the invention.

5.5. Establishment of Three Dimensional Cartilage Cultures in Vitro

The cells of the invention can be used to produce new cartilage tissue in vitro, which can then be implanted, transplanted or otherwise inserted into a site requiring cartilage tissue repair, replacement or augmentation in a subject.

In a non-limiting embodiment, the cells of the invention are used to produce a three-dimensional tissue construct in vitro, which is then implanted in vivo. As an example of the production of three-dimensional tissue constructs, see U.S. Pat. No. 4,963,489, issued Oct. 16, 1990, to Naughton et al., which is incorporated herein by reference. For example, the cells of the invention may be inoculated or "seeded" onto a three-dimensional framework or scaffold, and proliferated or grown in vitro to form a living cartilage tissue which can be implanted in vivo.

The cells of the invention can be grown freely in a culture vessel to sub-confluency or confluency, lifted from the culture and inoculated onto a three-dimensional framework. See Naughton et al., 1987, J. Med. 18:219–250, which is incorporated herein by reference. Inoculation of the three-dimensional framework with a high concentration of cells, e.g., approximately $10^6$ to $5 \times 10^7$ cells/ml, will result in the establishment of the three-dimensional support in relatively shorter periods of time.

The three-dimensional framework may be of any material and/or shape that: (a) allows cells to attach to it (or can be modified to allow cells to attach to it); and (b) allows cells to grow in more than one layer. A number of different materials may be used to form the matrix, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE, teflon), thermanox (TPX), nitrocellulose, cotton, polyglycolic acid (PGA), collagen (in the form of sponges, braids, or woven threads, etc.), cat gut sutures, cellulose, gelatin, or other naturally occurring bio-degradable materials or synthetic materials, including, for example, a variety of polyhydroxyalkanoates. Any of these materials may be woven into a mesh, for example, to form the three-dimensional framework or scaffold.

According to a preferred embodiment, the framework is a felt, which can be composed of a multifilament yarn made from a bioabsorbable material, e.g., PGA, PLA, polyglu-conate (PLGA) or hyaluronic acid. The yarn is made into a felt using standard textile processing techniques consisting of crimping, cutting, carding and needling. According to a further preferred embodiment, the felt is presoaked in a complete media and the porosity of the felt ranges from 80–98%, the density of the felt ranges from 30–60 mg/cc and the thickness of the felt ranges from 1–7 mm.

In addition, the three-dimensional framework may be molded into a useful shape, such as that of the external portion of the ear, or other specific structure in the body to be repaired, replaced or augmented.

Certain materials, such as nylon, polystyrene, etc., are poor substrates for cellular attachment. When these materials are used as the three-dimensional framework, it is advisable to pre-treat the matrix prior to inoculation of the cells of the invention in order to enhance their attachment to the matrix. For example, prior to inoculation with the cells of the invention, nylon matrices could be treated with 0.1M acetic acid and incubated in polylysine, PBS, and/or collagen to coat the nylon. Polystyrene could be similarly treated using sulfuric acid. Where the cultures are to be maintained for long periods of time or cryopreserved, non-degradable materials such as nylon, dacron, polystyrene, polyacrylates, polyvinyls, teflons, cotton, etc., may be preferred. A convenient nylon mesh which could be used in accordance with the invention is Nitex, a nylon filtration mesh having an average pore size of 210 µm and an average nylon fiber diameter of 90 µm (#3-210/36 Tetko, Inc., N.Y.).

In addition, the external surfaces of the three-dimensional framework may be modified to improve the attachment or growth of cells and differentiation of cartilage tissue, such as by coating the framework with one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, among others.

The cells of the invention are inoculated onto the framework. Since it is important to re-create in culture the cellular microenvironment found in vivo for cartilage, the extent to which the cells of the invention are grown prior to implantation in vivo or use in vitro may vary. In addition, growth factors such as TGF-β, with ascorbate, may be added to the culture medium prior to, during, or subsequent to inoculation of the cells to trigger chondrocyte differentiation and cartilage formation by the chondrocytes. The concentration of TGF-β maintained in the cultures can be monitored and adjusted to optimize growth.

Alternatively, the cells of the invention may be genetically engineered to express and produce for growth factors such as BMP-13 or TGF-β. For example, the gene or coding sequence for TGF-β would be placed in operative association with a regulated promoter so that production of TGF-β in culture can be controlled. The cells of the invention may be genetically engineered to produce other gene products beneficial to transplantation, e.g., anti-inflammatory factors, e.g., anti-GM-CSF, anti-TNF, anti-IL-1, anti-IL-2, etc. Alternatively, the cells may be genetically engineered to "knock out" expression of native gene products that promote inflammation, e.g., GM-CSF, TNF, IL-1, IL-2, or "knock out" expression of MHC in order to lower the risk of rejection. In addition, the cells may be genetically engineered for use in gene therapy to adjust the level of gene activity in a patient to assist or improve the results of the cartilage transplantation. The genetically engineered cells may then be screened to select those cell lines that: 1) bring about the amelioration of symptoms of rheumatoid disease or inflammatory reactions in vivo, and/or 2) escape immunological surveillance and rejection.

In addition to the cells of the invention, other cells may be added to the three-dimensional framework so as to improve the growth of, or alter, one or more characteristics of the new cartilage tissue formed thereon. Such cells may include, but are not limited to, fibroblasts, endothelial cells, pericytes, macrophages, monocytes, plasma cells, mast cells, adipocytes, etc, among others.

The three-dimensional framework may be modified so that the growth of cells and the production of cartilage tissue thereon is enhanced, or so that the risk of rejection of the implant is reduced. Thus, one or more biologically active compounds, including, but not limited to, anti-inflammatories, immunosuppressants or growth factors, may be added to the framework for local, sustained release. Examples of such sustained release formulations include composites comprising the biologically active compound and a biocompatible polymer, such as poly(lactic acid), poly(lactic-co-glycolic acid), methylcellulose, hyaluronic acid, collagen, and the like. The structure, selection and use of degradable polymers in drug delivery vehicles have been reviewed in several publications, including, A. Domb et al., 1992, Polymers for Advanced Technologies 3:279–292. Additional guidance in selecting and using polymers in pharmaceutical formulations can be found in the text by M. Chasin and R. Langer (eds.), 1990, "Biodegradable Polymers as Drug Delivery Systems, Vol. 45 of *Drugs and the Pharmaceutical Sciences*, M. Dekker, New York. These publications are incorporated by reference.

In yet another embodiment, the cells of the invention may be used in conjunction with a three-dimensional culture system in a "bioreactor" to produce cartilage tissue constructs which possess critical biochemical, physical and structural properties of native human cartilage tissue by culturing the cells and resulting tissue under environmental conditions which are typically experienced by native cartilage tissue. Thus, the three-dimensional culture system may be maintained under intermittent and periodic pressurization and the cells of the invention provided with an adequate supply of nutrients by convection. Maintaining an adequate supply of nutrients to the cells of the invention throughout a replacement cartilage tissue construct of approximately 2–5 mm thickness is extremely important as the apparent density of the construct increases. Pressure facilitates flow of fluid through the microporous three-dimensional cartilage construct, thereby improving the supply of nutrients and removal of waste from cells embedded in the construct. The bioreactor may include a number of designs including, but not limited to, the "piston-style" hard plastic bioreactor; bellows; soft plastic bag with "pressure plate"; and soft plastic bag with "roller pins".

After inoculation of the cells of the invention onto the three-dimensional framework, the cells on the framework are incubated in an appropriate culture medium. Many commercially available media, such as DMEM, RPMI 1640, Fisher's, Iscove's, McCoy's, and the like, may be suitable for use. Other useful culture media may be empirically formulated. Such culture media may be supplemented with one or more other components, such as FBS, ES, HS, and one or more antimicrobial compounds, including antibiotics and antimycotics, such as those listed supra, among others.

It is important that the three-dimensional framework be suspended or floated in the medium during the incubation period in order to maximize proliferative activity. In addition, the culture should be "fed" periodically to remove spent media, depopulate released cells, and add fresh media. The concentration of TGF-$\beta$, if present, may be adjusted during these steps. A concentration of about 10 ng/ml of TGF-$\beta$ is often desirable. In chondrocyte cultures, proline, a non-essential amino acid, and ascorbate (about 50 $\mu$g/ml) may also be included in the cultures.

These procedures are greatly facilitated when carried out using a bioreactor, which is a closed system housing the three-dimensional framework inoculated with the cells of the invention. A bioreactor reduces the possibility of contamination, and maintains the culture under intermittent and periodic pressurization to create environmental conditions that maintain an adequate supply of nutrients to the cells throughout the three-dimensional construct by convection.

During the incubation period, the cells of the invention generally grow linearly along and envelop and colonize the three-dimensional framework before beginning to grow into and across the openings or pores of the framework. The pores of the framework should be of an appropriate size to allow the cells of the invention to stretch across them. When using a mesh type of framework, pores ranging from about 150 $\mu$m to about 220 $\mu$m have been found to work satisfactorily. However, depending upon the three-dimensional structure and intricacy of the framework, other pore sizes may work equally well. In fact, any shape or structure that allows the cells of the invention to stretch and continue to replicate and grow for lengthy time periods will work in accordance with the invention.

During incubation of the three-dimensional framework with attached cells, proliferating cells may be released from the matrix. These released cells may stick to the walls of the culture vessel where they may continue to proliferate and form a confluent monolayer. This should be prevented or minimized, as for example by removal of the released cells during feeding or by transferring the three-dimensional framework to a new culture vessel. As described supra, the presence of a confluent monolayer in the vessel will tend to "shut down" the growth of cells in the three-dimensional framework and/or culture. Removal of the confluent monolayer or transfer of the framework to fresh media in a new vessel will usually restore proliferative activity of the three-dimensional culture system. Such removal or transfer should be done in any culture vessel which has a cellular monolayer exceeding 25% confluency. Alternatively, the culture vessel could be agitated, for example, on an orbital shaker, to prevent the released cells from sticking, or instead of periodically feeding the cultures, the culture system could be set up so that fresh media continuously flows through the system by convection. The flow rate could be adjusted to both maximize proliferation within the three-dimensional culture, and to wash out and remove cells released from the framework, so that they will not stick to the walls of the vessel and grow to confluence. In any case, the released cells can be collected and cryopreserved for future use.

5.6. Uses for New Cartilage Tissue

The cells and cartilage tissue of the present invention can be used in a variety of applications. These include, but are not limited to, transplantation or implantation of the cells either in unattached form or as attached, for example, to a three-dimensional framework, as described supra; or injection of extracellular matrix prepared from new cartilage tissue produced by the cells of the invention. Such cells, tissues and extracellular matrix may serve to repair, replace or augment cartilage tissue that has been damaged due to disease or trauma, or that failed to develop normally, or for cosmetic purposes.

In addition, the cells or cartilage tissue of the invention can be used: (1) to screen in vitro for the efficacy and/or cytotoxicity of compounds, allergens, growth/regulatory factors, pharmaceutical compounds, etc.; (2) to elucidate the mechanism of certain diseases; (3) to study the mechanism by which drugs and/or growth factors operate; (4) to diagnose and monitor cancer in a patient; (5) for gene therapy; and (6) to produce biologically active products, to name but a few uses.

5.6.1. Transplantation in Vivo

The cartilage tissue produced according to the invention can be used to repair or replace damaged or destroyed cartilage tissue, to augment existing cartilage tissue, to introduce new or altered tissue, to modify artificial prostheses, or to join biological tissues or structures. For example, and not by way of limitation, specific embodiments of the invention would include (i) hip prostheses coated with replacement cartilage tissue constructs grown in three-dimensional cultures; (ii) knee reconstruction with cartilage tissue constructs; (iii) prostheses of other joints requiring reconstruction and/or replacement of articular cartilage; and (iv) cosmetic reconstruction with cartilage tissue constructs.

For example, the evaluation of internal derangements of articular cartilage in several articulations, including the knee, hip, elbow, ankle and the glenohumeral joint, has been made possible by arthroscopic techniques. Arthroscopic surgery has become increasingly popular as well as successful, e.g., numerous small cutting tools, 3 to 4 mm in diameter, can be used in the knee. Triangulation, in which the operating instruments are brought into the visual field provided by the arthroscope, requires multiple portals of entry; alternatively, the cutting tools can be passed through a channel in the arthroscope itself in which case only one opening in the joint is necessary (Jackson, R. W., 1983, J. Bone Joint Surg. [AM] 65:416). Selective removal of the injured or deteriorated portion by arthroscopic surgery, followed by cartilage grafting, can be employed successfully. Cartilage tissue constructs can also be employed in major reconstructive surgery for different types of joints. Detailed procedures have been described in Resnick, D., and Niwayama, G., (eds), 1988, *Diagnosis of Bone and Joint Disorders,* 2d ed., W. B. Sanders Co., which is incorporated herein by reference.

The successful repair or replacement of damaged cartilage can be enhanced if the implanted cells and/or cartilage tissue can be fixed in place at the site of repair. Post-implantation joint movement may cause the new cells or cartilage tissue to become dislodged from the site if a pro-active fixation technique is not employed. Various methods can be used to fix the new cells and/or cartilage tissue in place, including: patches derived from biocompatible tissues, which can be placed over the site; bioabsorbable sutures or other fasteners, e.g., pins, staples, tacks, screws and anchors; non-absorbable fixation devices, e.g., sutures, pins, screws and anchors; adhesives; and the use of interference fit geometries.

5.6.2. Therapeutic Uses for Extracellular Matrix

As an alternative to implanting the cells of the invention, or living cartilage tissue produced therefrom, a subject in need of cartilage repair, replacement, or augmentation may benefit from the administration of the extracellular matrix ("ECM") produced by those cells or tissues. Thus, after the cells of the invention have been used to produce new cartilage tissue in vitro, such as, for example, by using the three-dimensional culture system described supra, such that a desired amount of ECM has been secreted onto the framework, the cells comprising the new tissue are removed, and the ECM processed for further use, for example, as an injectable preparation.

Accordingly, the cells comprising the new cartilage tissue may be killed and any cellular debris removed from the framework. This process may be carried out in a number of different ways. For example, the living cartilage tissue can be flash-frozen in liquid nitrogen without a cryopreservative, or the cartilage tissue can be immersed in sterile distilled water so that the cells burst in response to osmotic pressure.

Once the cells have been killed, the cellular membranes may be disrupted and cellular debris removed by treatment with a mild detergent rinse, such as EDTA, CHAPS or a zwitterionic detergent. An advantage to using a mild detergent rinse is that it solubilizes membrane-bound proteins, which are often highly antigenic.

Alternatively, the cartilage tissue can be enzymatically digested and/or extracted with reagents that break down cellular membranes and allow removal of cell contents. Example of such enzymes include, but are not limited to, nucleases (for example, deoxyribonuclease and ribonuclease), phospholipases and lipases. Examples of detergents include non-ionic detergents such as, for example, TRITON X-100, octylphenoxy polyethoxy-ethanol (Rohm and Haas), BRIJ-35, a polyethoxyethanol lauryl ether (Atlas Chemical Co.), TWEEN 20, a poly-ethoxyethanol sorbitan monolaureate (Rohm and Haas), LUBROL-PX, or polyethylene lauryl ether (Rohm and Haas); and ionic detergents such as, for example, sodium dodecyl sulphate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending on whether the new cartilage tissue has been formed on a three-dimensional framework that is biodegradable or non-biodegradable. For example, if the framework is non-biodegradable, the ECM can be removed by subjecting the framework to sonication, high pressure water jets, mechanical scraping or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM produced by the chondrocytes of the invention.

Once the ECM has been collected, it may be processed further. The ECM can thus be homogenized to fine particles using techniques well known in the art such as, for example, by sonication, so that they can pass through a surgical needle. The components of the ECM can be cross-linked, if desired, by gamma irradiation. Preferably, the ECM can be irradiated between 0.25 to 2M rads to sterilize and cross-link the ECM. Chemical cross-linking using agents which are toxic, such as glutaraldehyde, is possible but not generally preferred.

The amounts and/or ratios of proteins, such as the various types of collagen present in the ECM, may be adjusted by mixing the ECM produced by the cells of the invention with ECM secreted by one or more other cell types. In addition, biologically active substances such as proteins, growth factors and/or drugs, can be incorporated into the ECM preparation. Exemplary biologically active substances include tissue growth factors, such as TGF-$\beta$, and the like, which promote healing and tissue repair at the site of the injection.

Formulation of ECM for administration to a subject will typically involve adjusting the ionic strength of the preparation to isotonicity (i.e., about 0.1 to 0.2) and to physiological pH (i.e., about pH 6.8 to 7.5). In addition, a local anesthetic, such as lidocaine (usually at a concentration of about 0.3% by weight), may be added to reduce local pain upon injection. In addition, the ECM formulation may comprise a pharmaceutically acceptable carrier. A variety of aqueous carriers may be used, such as water, buffered water, 0.4% saline, 0.3% glycine, and the like. The ECM formulation may also comprise additional components that serve to extend the shelf-life of a pharmaceutical formulation, including preservatives, protein stabilizers, and the like. The ECM formulation is preferably sterile and free of particulate matter (for injectable forms). The ECM formulation may be sterilized by conventional, well-known sterilization techniques. The ECM formulation may contain pharmaceutically acceptable auxiliary substances as required to approximate physiological conditions, such as pH adjusting and buffering agents, toxicity adjusting agents and the like, e.g., sodium acetate, sodium chloride, potassium chloride, calcium chloride, sodium lactate, etc.

The ECM formulation may be adapted for various forms of administration, including subcutaneously, and the like. Actual methods for preparing administrable compositions and adjustments necessary for administration to subjects will be known or apparent to those skilled in the art and are described in more detail in, for example, Remington's *Pharmaceutical Science.* 17*th Ed.*, Mack Publishing Company, Easton, Pa. (1985), which is incorporated herein by reference.

The ECM formulation may also contain a fluid lubricant that can be tolerated by the body. Such lubricants are generally used to improve the injectability, intrudability and dispersion of the ECM at the site of injection and to decrease the amount of spiking by modifying the viscosity of the compositions. Spiking can cause the composition to ooze from the syringe rather than be injected into the tissue. Exemplary lubricants include glycerol, glycogen, maltose and the like. Organic polymer base materials such as polyethylene glycol, hyaluronic acid, and non-fibrillar collagen, including succinylated collagen, can also act as lubricants.

The final ECM formulation may then be placed in a syringe or other injection apparatus for precise placement of the matrix at the site of a tissue defect or where augmentation is otherwise desired. In the case of formulations for dermal augmentation, the term "injectable" means the formulation can be dispensed from syringes having a gauge as low as 25 under normal conditions under normal pressure without substantial spiking. For this precise placement, needles as fine as 27 gauge ($200\mu$ I.D.) or even 30 gauge ($150\mu$ I.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle.

The above described process for preparing injectable ECM is preferably carried out under sterile conditions using sterile materials. The processed ECM in a pharmaceutically acceptable carrier can be injected intradermally or subcutaneously to augment soft tissue or to repair or correct congenital anomalies, acquired defects or cosmetic defects. Examples of such conditions are congenital anomalies such as hemifacial microsomia, malar and zygomatic hypoplasia, unilateral mammary hypoplasia, pectus excavatum, pectoralis agenesis (Poland's anomaly) and velopharyngeal incompetence secondary to cleft palate repair or submucous cleft palate (as a retropharyngeal implant); acquired defects (post-traumatic, post-surgical, post-infectious) such as depressed scars, subcutaneous atrophy (e.g., secondary to discoid lupus erythematosus), keratotic lesions, enophthalmos in the unucleated eye (also superior sulcus syndrome), acne pitting of the face, linear scleroderma with subcutaneous atrophy, saddle-nose deformity, Romberg's disease and unilateral vocal cord paralysis; and cosmetic defects such as glabellar frown lines, deep nasolabial creases, circum-oral geographical wrinkles, sunken cheeks and mammary hypoplasia. The processed ECM in a pharmaceutically acceptable carrier can also be injected into internal tissues, such as the tissues defining body sphincters to augment such tissues.

5.6.3. Screening Effectiveness and Cytotoxicity of Compounds in Vitro

The cells and cartilage tissues of the invention may be used in vitro to screen a wide variety of compounds for effectiveness and cytotoxicity of pharmaceutical agents, growth/regulatory factors, anti-inflammatory agents, etc. To this end, the cells of the invention, or tissue cultures described above, are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the number of living cells in vitro, e.g., by total cell counts, and differential cell counts. This may be accomplished using standard cytological and/or histological techniques, including the use of immunocytochemical techniques employing antibodies that define type-specific cellular antigens. The effect of various drugs on the cells of the invention either in suspension culture or in the three-dimensional system described above may be assessed.

The cells and cartilage tissues of the invention may be used as model systems for the study of physiological or pathological conditions. For example, joints that are immobilized suffer relatively quickly in a number of respects. The metabolic activity of chondrocytes appears affected as loss of proteoglycans and an increase in water content are soon observed. The normal white, glistening appearance of the cartilage changes to a dull, bluish color, and the cartilage thickness is reduced. However, the amount of this change that is due to nutritional deficiency versus the amount due to upset in the stress-dependent metabolic homeostasis is not yet clear. The cells and cartilage tissues of the invention may be used to determine the nutritional requirements of cartilage under different physical conditions, e.g., intermittent pressurization, and by pumping action of nutrient medium into and out of the cartilage construct. This may be especially useful in studying underlying causes for age-related or injury-related decrease in tensile strength of articular cartilage, e.g., in the knee, that predispose the weakened cartilage to traumatic damage.

The cells and cartilage tissues of the invention may also be used to study the mechanism of action of cytokines and other pro-inflammatory mediators, e.g., IL-1, TNF and prostaglandins, that are released into the synovial fluid as a result of rheumatic disease. Thus, the patient's own joint fluid could be tested in vitro to study the effects of these compounds on growth of the cells of the invention. In addition, cytotoxic and/or pharmaceutical agents can be screened for those that are most efficacious for a particular patient, such as those that reduce or prevent resorption of cartilage or otherwise enhance the balanced growth of articular cartilage. Agents which prove to be efficacious in vitro could then be used to treat the patient therapeutically.

5.7. Genetically Engineered Chondrocytes and Cartilage

The cells and cartilage tissues of the present invention may afford a vehicle for introducing genes and gene products in vivo to assist or improve the results of implantation and/or for use in gene therapies. The following description is directed to the genetic engineering of any of the cells of the invention or tissues produced therefrom.

Cells which express a gene product of interest, or cartilage tissue produced in vitro therefrom, can be implanted into a subject who is otherwise deficient in that gene product. For example, genes that express a product capable of preventing or ameliorating symptoms of various types of rheumatoid or joint diseases, such as those involved in preventing inflammatory reactions, may be under-expressed or down-regulated under disease conditions. Alternatively, the activity of gene products may be diminished, leading to the manifestation of some or all of the pathological conditions associated with rheumatoid or joint disease. In either case, the level of active gene product can be increased by gene therapy, i.e., by genetically engineering cells of the invention to produce active gene product and implanting the engineered cells, or tissues made therefrom, into a subject in need thereof.

In one embodiment, the cells of the invention are genetically engineered to express an anti-inflammatory gene product that would serve to reduce the risk of failure of implantation or further degenerative change in cartilage tissue due to rheumatoid disease or inflammatory reaction. For example, the cells of the invention can be genetically engineered to express one or more anti-inflammatory gene products including, for example, peptides or polypeptides corresponding to the idiotype of antibodies that neutralize granulocyte-macrophage colony stimulating factor (GM-CSF), TNF, IL-1, IL-2, or other inflammatory cytokines. IL-1 has been shown to decrease the synthesis of proteoglycans and collagens type II, IX, and XI (Tyler et al., 1985, Biochem. J. 227:869–878; Tyler et al., 1988, Coll. Relat. Res. 82:393–405; Goldring et al., 1988, J. Clin. Invest. 82:2026–2037; and Lefebvre et al., 1990, Biophys. Acta. 1052:366–372). TNF also inhibits synthesis of proteoglycans and type II collagen, although it is much less potent than IL-1 (Yaron, I., et al., 1989, Arthritis Rheum. 32:173–180; Ikebe, T., et al., 1988, J. Immunol. 140:827–831; and Saklatvala, J., 1986, Nature 322:547–549). Alternatively, the cells of the invention can be genetically engineered to produce a gene product that would serve to stimulate cartilage production such as, for example, BMP-13 or TGF-$\beta$. Also, for example, the cells of the invention may be engineered to express the gene encoding the human complement regulatory protein which prevents rejection of a graft by the host. See, for example, McCurry et al., 1995, Nature Medicine 1:423–427.

Methods that may be useful to genetically engineer the cells of the invention are well-known in the art. For example, a recombinant DNA construct or vector containing the gene of interest may be constructed and used to transform or transfect one or more cells of the invention. Such transformed or transfected cells that carry the gene of interest, and that are capable of expressing said gene, are selected and clonally expanded in culture. Methods for preparing DNA constructs containing the gene of interest, for transforming or transfecting cells, and for selecting cells carrying and expressing the gene of interest are well-known in the art. See, for example, the techniques described in Maniatis et al., 1989, *Molecular Cloning, A Laboratory Manual*, Cold Spring Harbor Laboratory Press, Cold Spring Harbor, N.Y.; Ausubel et al., 1989, *Current Protocols in Molecular Biology*, Greene Publishing Associates & Wiley Interscience, N.Y.; and Sambrook et al., 1989, *Molecular Cloning: A Laboratory Manual,* 2nd Ed., Cold Spring Harbor Laboratory Press, Cold Spring Harbor, N.Y. In addition, the transkaryotic implantation technique described by Seldon et al., 1987, Science 236:714–718, may be useful. All of these publications are incorporated herein by reference.

The cells of the invention can be engineered using any of a variety of vectors including, but not limited to, integrating viral vectors, e.g., retrovirus vector or adeno-associated viral vectors, or non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by, i.e., in operative association with, one or more appropriate expression control elements such as promoter or enhancer sequences, transcription terminators, polyadenylation sites, among others, and a selectable marker. Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines which express the gene product.

Any promoter may be used to drive the expression of the inserted gene. For example, viral promoters include but are not limited to the CMV promoter/enhancer, SV 40, papillomavirus, Epstein-Barr virus, elastin gene promoter and $\beta$-globin. Preferably, the control elements used to control expression of the gene of interest should allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock protein.

Examples of transcriptional control regions that exhibit tissue specificity which have been described and could be used include but are not limited to: elastase I gene control region, which is active in pancreatic acinar cells (Swit et al., 1984, Cell 38:639–646; Ornitz et al., 1986, Cold Spring Harbor Symp. Quant. Biol. 50:399–409; MacDonald, 1987, Hepatology 7:425–515); insulin gene control region, which is active in pancreatic beta cells (Hanahan, 1985, Nature 315:115–122); immunoglobulin gene control region, which is active in lymphoid cells (Grosschedl et al., 1984, Cell 3S:647–658; Adams et al., 1985, Nature 318:533–538; Alexander et al., 1987, Mol. Cell. Biol. 7:1436–1444); myelin basic protein gene control region, which is active in oligodendrocyte cells in the brain (Readhead et al., 1987, Cell 48:703–712); myosin light chain-2 gene control region, which is active in skeletal muscle (Shani, 1985, Nature 314:283–286); and gonadotropic releasing hormone gene control region, which is active in the hypothalamus (Mason et al., 1986, Science 234:1372–1378).

The cells of the invention may be genetically engineered to "knock out" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a chondrocyte can be reduced or knocked out using a number of techniques including, for example, inhibition of expression by inactivating the gene completely (commonly termed "knockout") using the homologous recombination technique. Usually, an exon encoding an important region of the protein (or an exon 5' to that region) is interrupted by a positive selectable marker, e.g., neo, preventing the production of normal MRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, Proc. Nat. Acad. Sci. U.S.A. 88:3084–3087).

Antisense and ribozyme molecules which inhibit expression of the target gene can also be used in accordance with the invention to reduce the level of target gene activity. For example, antisense RNA molecules which inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, *Basic Methods in Molecular Biology,* 2nd ed., Appleton & Lange, Norwalk, Conn., which is incorporated herein by reference.

Using any of the foregoing techniques, the expression of IL-1 can be knocked out in the cells of the invention to reduce the risk of resorption of implanted cartilage or the production of inflammatory mediators by the cells of the invention. Likewise, the expression of MHC class II molecules can be knocked out in order to reduce the risk of rejection of the implanted tissue.

Once the cells of the invention have been genetically engineered, they may be directly implanted into the patient to allow for the amelioration of the symptoms of rheumatoid or joint disease by producing an anti-inflammatory gene product such as, for example, peptides or polypeptides corresponding to the idiotype of neutralizing antibodies for GM-CSF, TNF, IL-1, IL-2, or other inflammatory cytokines. IL-1 is a potent stimulator or cartilage resorption and of the production of inflammatory mediators by chondrocytes (Campbell et al., 1991, J. Immun. 147:1238–1246). Alternatively, the genetically engineered cells may be used to produce new cartilage tissue in vitro, which is then implanted in the subject, as described supra.

The use of the compositions and methods of the invention in gene therapy has a number of advantages. Firstly, since the culture comprises eukaryotic cells, the gene product will likely be properly expressed and processed to form an active product. Secondly, gene therapy techniques are generally useful where the number of transfected cells can be substantially increased to be of clinical value, relevance, and utility. Thus, for example, the three-dimensional culture described supra allows for mitotic expansion of the number of transfected cells and amplification of the gene product to levels that may be efficacious in treating joint disease.

5.8. Production of Biological Molecules

In a further embodiment, the cells of the invention can be cultured in vitro to produce biological products in high yield. For example, such cells, which either naturally produce a particular biological product of interest (e.g., a growth factor, regulatory factor, or peptide hormone etc.), or have been genetically engineered to produce a biological product, could be clonally expanded using, for example, the three-dimensional culture system described above. If the cells excrete the biological product into the nutrient medium, the product can be readily isolated from the spent or conditioned medium using standard separation techniques, e.g., such as differential protein precipitation, ion-exchange chromatography, gel filtration chromatography, electrophoresis, and HPLC, to name but a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells are lysed. The biological product may then be purified using any one or more of the above-listed techniques.

6. EXAMPLE

Isolation of Pre-Chondrocytes from Wharton's Jelly and Induction of Cartilage Tissue

6.1. Materials and Methods

Human umbilical cord was obtained immediately after the conclusion of a full term pregnancy. Wharton's jelly was excised from the umbilical cord under sterile conditions, cut into tissue sections of approximately 2–3 mm$^3$, and about 50–100 tissue sections placed in a 100 mm TC-treated Petri dish containing sterile glass slides on the bottom of the Petri dish. A glass slide was placed over each tissue section, in effect sandwiching the cells between the slides, and tapped lightly to ensure good contact between the tissue section and the Petri dish. The tissue sections were flooded with 20 ml of complete medium (i.e., RPMI 1640, 10% FBS, 5% ES, penicillin G (100 µg/ml), streptomycin sulfate (100 µg/ml), amphotericin B (250 µg/ml), gentamicin (10 µg/ml)), pH 7.4–7.6, without dislodging the slides. The tissue sections were incubated at 37° C. and 5% $CO_2$ and the medium was changed twice per week.

After 10–12 days, the original tissue sections were removed, and the cells attached to the slides and the Petri dish were trypsinized using standard techniques. After trypsinization, the cells were collected and removed to fresh medium in a T175 flask at an initial cell density of about 0.75–1.0×10$^6$ cells and incubated as above. The medium was changed at 24 hr post-trypsinization to remove floating cells. The pre-chondrocytes were then passaged three times on complete culture medium to a final cell density each time of 3 to 6.5×10$^4$ cells/cm$^2$.

After completion of the third passage, the pre-chondrocytes were transferred to a "freeze medium" comprising complete culture medium and 10% DMSO, at a density of about 4–10×10$^6$ cells/ml. The freezing medium was placed at 4° C. prior to the addition of the cells, thereafter, the cells remained in the medium for a few minutes at 4° C. to equilibrate prior to freezing. The cells were dispensed into plastic ampoules (Nunc, Naperville, Md.) which were sealed and transferred to the freezing chamber of a programmable freezer (770 Cryomed). The freezing program reduced the temperature at a rate of −1° C./min through the heat of fusion. The ampoules were then transferred to a liquid nitrogen storage area. Cells were thawed rapidly by transferring an ampoule from liquid nitrogen to a 37° C. water bath. The thawed contents of the ampoule were immediately transferred under sterile conditions to a culture vessel containing complete medium. The initial cell density in the culture medium was adjusted to about $3-6 \times 10^5$ cells/ml. Once in culture, the cells were examined with an inverted microscope to detect cell proliferation, and were passaged to fresh medium when they reached a density of about $3-6.5 \times 10^4$ cells/cm$^2$.

After mitotic expansion of not more than approximately four passages from initiation of primary culture, approximately $4 \times 10^6$ cells were seeded onto a three-dimensional framework, as described infra.

A three-dimensional framework comprising PGA-felt was generated using PGA fibers (Albany International, Mansfield, Mass.) having a thickness of about $13 \pm 1$ µm. The PGA fibers were assembled into a construct of 1 cm diameter and 2 mm thickness, having a density of $1.50-1.64$ gm/cm$^3$ and weighing $5.5-6.5$ mg (porosity $\cong 97\%$). The PGA felt construct was sterilized using an electron beam.

The PGA felt construct was presoaked in complete culture medium, comprising RPMI 1640 containing 10% FBS and 5% ES by placing the PGA felt construct in a sterile vessel containing enough medium to cover it, and flooding all sections of the PGA felt construct with the medium using a pipette. The PGA felt construct was incubated in culture medium at 37° C. for 2 hr.

Each well of a 12-well sterile culture plate (Corning Glassworks, N.Y.) was coated with 1.5 ml of 1% agarose (FMC Bioproducts, Rockville, Md.) which was allowed to gel, and 1 ml complete medium plus ascorbate (50 µg/ml) was added to each well. The agarose is used to capture any cells that fall off the felt to prevent them from forming monolayers which could inhibit cell growth on the felt. The cells of the invention were suspended in complete medium with ascorbate to a density of about $4 \times 10^7$ cells/ml. The PGA felt construct was removed from the medium, allowed to dry, and seeded with cells of the invention by applying 100 µl of cell suspension ($4 \times 10^6$ cells/ml) to the dry PGA felt construct with a pipette. The cell-seeded PGA felt construct was then placed into the medium within each well. The culture plate containing the cell-seeded PGA felt construct was incubated at 37° C. for 2 hr on an orbital shaker (100 rpm), 4 ml complete medium with ascorbate was added, and the culture plate was incubated as above for 3 days. The cell-seeded PGA-felt construct was then removed to a new well of a 6-well culture dish without agarose, but containing complete medium with ascorbate and TGF-β1 (10 ng/ml), and cultured for 72 hr. The cell-seeded PGA felt construct was then removed to a well containing complete medium without TGF-β1 and cultured for three weeks with the medium replaced every three days.

At the end of the culture period, cell-seeded PGA felt constructs were fixed in 10% neutral buffered formalin, embedded in paraffin, and sectioned (4–6 µm). Sections were stained with either hematoxylin/eosin (FIGS. 2A–B), alcian blue, ruthenium red, safranin O (FIG. 3A), or trichrome (FIG. 3B), or with immunoperoxidase after labeling with anti-collagen I or II antibodies (FIGS. 4A–4E).

6.2. Results

At the end of the three-week incubation period, cell-seeded PGA felt constructs that had been exposed to the TGF-β1 pulse had produced a "tissue" that was hard, glistening, and had the consistency of cartilage tissue (FIGS. 1A and 1B) while the cell-seeded PGA felt constructs that had not been exposed to TGF-β1 also produced a "tissue" with cartilage specific properties, it was smaller and less dense than the TGF-β1 treated cells (FIG. 1C). Immunostaining showed the deposition of both collagen I and collagen II (FIGS. 4A–4E).

All patents, patent applications, and publications cited above are incorporated herein by reference.

The present invention is not to be limited in scope by the specific embodiments described which are intended as single illustrations of individual aspects of the invention. Functionally equivalent methods and compositions, in addition to those shown and described herein, will become apparent to those skilled in the art from the foregoing description and accompanying drawings. Such modifications are intended to fall within the scope of the appended claims.

What is claimed is:

1. A method of isolating a pre-chondrocyte from Wharton's jelly of the umbilical cord comprising, collecting Wharton's jelly comprising pre-chondrocytes from an umbilical cord, culturing the Wharton's jelly in vitro under conditions wherein said pre-chondrocytes proliferate, and isolating the pre-chondrocyte therefrom.

2. The method of claim 1, further comprising culturing the prechondrocytes in a culture medium containing one or more growth factors, wherein the pre-chondrocytes undergo mitotic expansion.

3. A method of isolating a chondrocyte from Wharton's jelly of the umbilical cord comprising, collecting Wharton's jelly comprising pre-chondrocytes from an umbilical cord, culturing the Wharton's jelly in vitro under conditions wherein said pre-chondrocytes proliferate, isolating the pre-chondrocytes therefrom, culturing the pre-chondrocytes under conditions that induce the production of chondrocytes capable of producing cartilage tissue, and isolating the chondrocyte.

4. The method of claim 3, wherein the pre-chondrocytes are cultured in a culture medium containing one or more growth factors, wherein the pre-chondrocytes undergo mitotic expansion.

5. The method of claim 3, further comprising culturing the chondrocyte in a culture medium containing one or more growth factors, wherein the chondrocytes undergo mitotic expansion.

6. The method of claim 3, wherein the chondrocyte cells are capable of secreting an extracellular matrix.

* * * * *